US010149876B2

(12) United States Patent
Chow et al.

(10) Patent No.: US 10,149,876 B2
(45) Date of Patent: Dec. 11, 2018

(54) *TRIPTERYGIUM WILFORDII* EXTRACTS TO OVERCOME CHEMOTHERAPY RESISTANCE

(71) Applicant: WESTERN UNIVERSITY OF HEALTH SCIENCES, Pomona, CA (US)

(72) Inventors: Moses Sing Sum Chow, Chino Hills, CA (US); Ying Huang, Arcadia, CA (US); Jinghua Jeffrey Wang, Arcadia, CA (US); Ranadheer Ravula, Atlanta, GA (US); Zhi Jun Wang, Chino Hills, CA (US)

(73) Assignee: WESTERN UNIVERSITY OF HEALTH SCIENCES, Pomona, CA (US)

( * ) Notice: Subject to any disclaimer, the term of this patent is extended or adjusted under 35 U.S.C. 154(b) by 561 days.

(21) Appl. No.: 14/422,216

(22) PCT Filed: Aug. 19, 2013

(86) PCT No.: PCT/US2013/055602
§ 371 (c)(1),
(2) Date: Feb. 18, 2015

(87) PCT Pub. No.: WO2014/031543
PCT Pub. Date: Feb. 27, 2014

(65) Prior Publication Data
US 2015/0238553 A1 Aug. 27, 2015

Related U.S. Application Data

(60) Provisional application No. 61/684,792, filed on Aug. 19, 2012.

(51) Int. Cl.
*A61K 36/00* (2006.01)
*A61K 36/37* (2006.01)
*A61K 31/337* (2006.01)
*A61K 31/517* (2006.01)
*A61K 31/704* (2006.01)
*A61K 39/395* (2006.01)

(52) U.S. Cl.
CPC ............ *A61K 36/37* (2013.01); *A61K 31/337* (2013.01); *A61K 31/517* (2013.01); *A61K 31/704* (2013.01); *A61K 39/3955* (2013.01); *A61K 39/39558* (2013.01)

(58) Field of Classification Search
CPC ...................................................... A61K 36/00
See application file for complete search history.

(56) References Cited

U.S. PATENT DOCUMENTS 5,916,564 A   6/1999 Lipsky et al.

FOREIGN PATENT DOCUMENTS

| CN | 102443039 A | 5/2012 |
| EP | 1604661 A1 | 12/2005 |
| JP | 2004/075888 A1 | 6/2006 |

OTHER PUBLICATIONS

Chen et al, Triptolide circumvents drug-resistant effect and enhances 5-fluorouracil antitumor effect on KB cells. Anti-Cancer Drugs, (Jun. 2010) vol. 21, No. 5, pp. 502-513.*
Li, Synergistic anticancer activity of triptolide combined with cisplatin enhances apoptosis in gastric cancer in vitro and in vivo. Cancer letters, (Jun. 28, 2012) vol. 319, No. 2, pp. 203-213 (Year: 2012).*
Ravula et al, Bioassay-guided identification of novel P-glycoprotein inhibitors from traditional Chinese medicines. Cancer Research, (Apr. 15, 2010) vol. 70, No. 8, Supp. SUPPL (Year: 2010).*
Extended European Search Report in corresponding EP Application No. 13831724, dated Mar. 8, 2016.
Chia-Jung et al., "Synergistic anticancer activity of triptolide combined with cisplatin enhances apoptosis in gastric cancerand," Cancer Letters, vol. 319, No. 2, Jan. 10, 2012, pp. 203-213.
Ranadheer et al., "Extract of Triptergium wilfordii sensitizes drug resistant prostate cancer cells to docetaxel," J. of Clinical Pharm., Sep. 9, 2011, vol. 51, No. 9, p. 1364.
Xiao-Yan Tang et al., "Synergistic effect of triptolide combined with 5-fluorouracil on colon carcinoma," Postgraduate Medical Journal, vol. 83, No. 979, May 2007, pp. 338-343.
International Search Report and Written Opinion in PCT Application No. PCT/US2013/055602 dated Jan. 17, 2014.
International Preliminary Report on Patentability in PCT Application No. PCT/US2013/055602 dated Mar. 5, 2015.
Chen et al.: "Triptolide Circumvents Drug-Resistant Effect and Enhances 5-Fluorouracil Antitumor Effect on KB Cells," Anti-Cancer Drugs, vol. 21, pp. 502-513, 2010.
Li et al.: "Modulation of P-Glycoprotein Expression by Triptolide in Adriamycin-Resistant K562/A02 Cells," Oncology Letters, vol. 3, pp. 485-489, 2012.

(Continued)

Primary Examiner — Qiuwen Mi
(74) Attorney, Agent, or Firm — J.A. Lindeman & CO., PLLC

(57) ABSTRACT

The invention provides extracts and compositions derived from *Tripterygium wilfordii* for overcoming drug resistance in cancer therapy. This invention relates to organic solvent extracts of *T. wilfordii* and their use in cancer treatment, particularly in the treatment of cancers which have exhibited resistance to treatment by chemotherapeutic drugs. Methods of treating a cancer are disclosed. The method administers to a patient in need thereof a combination of (a) an organic solvent extract of *T. wilfordii* and (b) a chemotherapeutic drug. The organic solvent extract of *T. wilfordii* (a) and chemotherapeutic drug (b) are administered in a combined amount effective to treat the cancer. The cancer being treated is at least in part resistant to treatment by the chemotherapeutic drug (b) alone. Also disclosed are chemotherapeutic compositions comprising a combination of (a) an organic solvent extract of *T. wilfordii* and (b) a chemotherapeutic drug, wherein (a) and (b) are administered in a combined amount effective to treat the cancer; and a pharmaceutically acceptable carrier.

5 Claims, 18 Drawing Sheets

(56) References Cited

OTHER PUBLICATIONS

Liu et al.: "The Main Anticancer Bullets of the Chinese Medicinal Herb, Thunder God Vine," Molecules, vol. 16, pp. 5283-5297, Jun. 23, 2011.
Spivey et al.: "Celastraceae Sesquiterpenoids: Biological Activity and Synthesis," Chemical Society Reviews, vol. 31, pp. 43-59, Dec. 13, 2001.
English Language Abstract of CN 102443039A, publication date May 9, 2012.

* cited by examiner

TRIPTERYGIUM WILFORDII EXTRACTS TO OVERCOME CHEMOTHERAPY RESISTANCE

CROSS-REFERENCE TO RELATED APPLICATIONS

This application claims priority to U.S. Application Ser. No. 61/684,792, filed 19 Aug. 2012, and includes its disclosure herein by reference.

FIELD OF THE INVENTION

The invention relates to compounds and natural substances that enhance the effectiveness of chemotherapeutic drugs.

BACKGROUND

Drug resistance invariably develops over the course of continuing chemotherapy. Overcoming this problem is a major challenge in the treatment of cancer. Indeed, tumor cells utilize multiple mechanisms to increase their resistance to chemotherapeutic drugs. For example, tumor cells may overexpress the multiple drug resistant transporter and onco-protein epidermal growth factor receptor genes, as well as induce the activity of NF-E2-related factor 2, a redoxsensing transcription factor that upregulates a wide spectrum of genes involved in glutathione metabolism and drug detoxification. See (Huang et al., 2005a; Makarovskiy et al., 2002; Wang et al., 2010); (Salzberg et al., 2007; Sirotnak et al., 2000); (Singh et al., 2010; Zhang et al., 2010); and (Huang and Sadee, 2003; Seruga et al., 2010). The Hedgehog pathway is another cell signaling pathway that is involved in chemoresitance. (DomingoDomenech et al., 2012).

To date, no single agent that was designed to target a specific mechanism of resistance has been found to be effective. However, one potential source of novel therapies for addressing drug resistance are traditional Chinese herbal medicines. Indeed, such medicines have been used for thousands of years to restore imbalances of body functions that result from a multitude of diseases. Treatment with herbal medicines usually involve ingestion of a herbal "extract" that contains multiple chemical components that can potentially act at different sites and pathways in the body. Thus, these medicines have the potential to target multiple cellular and molecular mechanisms that may offer a new opportunities in overcoming drug resistance, or simply improve the efficacy of drugs. See Chow & Huang 2010, Pon et al 2010. As described herein, an ethanol extract from one particular traditional Chinese medicinal herb, *Triperygium wilfordii*, which is also known by its Chinese (Mandarin) name, Lei Gong Teng, sensitizes cancer cells that have become resistant to chemotherapeutic drug therapy, so that the cancer once again becomes sensitive to the chemotheapeutic drug.

SUMMARY OF THE INVENTION

This invention relates to organic solvent extracts of *Tripterygium wilfordii* and their use in cancer treatment, particularly in the treatment of cancers which have exhibited some resistance to treatment by chemotherapeutic drugs. Of the organic solvent extracts of *Tripterygium wilfordii* useful in the various embodiments of the extract may be (i) an ethanol extract; and identifiable by the MS/LC chromatogram as described in FIG. 1.

In one embodiment, the invention relates to a method of treating a cancer. The method administers to a patient in need thereof a combination of (a) an organic solvent extract of *Tripterygium wilfordii* and (b) a chemotherapeutic drug. The organic solvent extract of *Tripterygium wilfordii* (a) and chemotherapeutic drug (b) are administered in a combined amount effective to treat the cancer. The cancer being treated is at least in part resistant to treatment by the chemotherapeutic drug (b) alone. In an embodiment of the invention, the method administers (a) in an amount to increase (b)'s efficacy over the efficacy of (b) when administered alone. In embodiments of the invention, the cancer may be breast cancer, leukemia or prostate cancer and the chemotherapeutic drug (b) a drug current used to treat such cancers, e.g., docetaxel, daurorubicin, trastuzumab, and lapatinib.

The organic solvent extract of *Tripterygium wilfordii* (a) and chemotherapeutic drug (b) may be administered sequentially or co-administered. When they are administer sequentially, at least a portion of (a) is administered prior to administration of (b). The organic solvent extract of *Tripterygium wilfordii* (a) may be administered in the same manner and using a similar or the same chemotherapeutic composition. As noted above, in a method of the invention the organic solvent extract of *Tripterygium wilfordii* (a) and chemotherapeutic drug (b) may be co-administered and that may be in a single composition containing both (a) and (b). Accordingly, another embodiment of the invention relates to a chemotherapeutic composition comprising a combination of (a) an organic solvent extract of *Tripterygium wilfordii* and (b) a chemotherapeutic drug, wherein (a) and (b) are administered in a combined amount effective to treat the cancer; and a pharmaceutically acceptable carrier.

BRIEF DESCRIPTION OF THE TABLES

Table 1 reports the results of a the sulforhodamine B (SRB) cell viability assay of docetaxel-resistant PC3-TxR cells that were pre-treated with 12 µg/ml of Lei Gong Teng extract (LGT-E), followed by 72 hours of treatment with various concentrations of docetaxel.

Table 2 reports the results of a an SRB cell viability assay of docetaxel-resistant PC3-TxR cells after 72 hours of treatment with various concentrations of docetaxel and no pre-treatment with LGT-E.

Table 3 reports the results of an SRB cell viability assay of docetaxel-resistant PC3-TxR cells that were pre-treated with 25 µg/ml of LGT-E, followed by 72 hours of treatment with various concentrations of docetaxel.

Table 4 reports the results of an SRB cell viability assay of docetaxel-resistant PC3-TxR cells after 72 hours of treatment with various concentrations of docetaxel and no pre-treatment with LGT-E.

Table 5 reports the results of an SRB cell viability assay of docetaxel-resistant DU145-TxR cells that were pre-treated with 50 µg/ml of LGT-E, followed by 72 hours of treatment with various concentrations of docetaxel.

Table 6 reports the results of an SRB cell viability assay of docetaxel-resistant DU145-TxR cells after 72 hours of treatment with various concentrations of docetaxel and no pre-treatment with LGT-E.

Table 7 reports the results of an SRB cell viability assay of docetaxel-resistant DU145-TxR cells that were pre-treated with 25 µg/ml LGT-E followed by 72 hours of treatment with various concentrations of docetaxel.

Table 8 reports the results of an SRB cell viability assay of docetaxel-resistant DU145-TxR cells after 72 hours of treatment with various concentrations of docetaxel and no pre-treatment with LGT-E.

Table 9 reports the results of a sul-forhodamine B (SRB) cell viability assay of docetaxel-resistant DU145-TxR cells that were pre-treated with 12.5 μg/ml LGT-E followed by 72 hours of treatment with various concentrations of docetaxel.

Table 10 reports the results of an SRB cell viability assay of docetaxel-resistant DU145-TxR cells after 72 hours of treatment with various concentrations of docetaxel and no pre-treatment with LGT-E.

Table 11 reports the results of an SRB cell viability assay of docetaxel-resistant PC3-TxR cells after 72 hours of treatment with various concentrations of docetaxel or no pre-treatment with LGT-E.

Table 12 reports the results of an SRB cell viability assay of docetaxel-sensitive PC3 cells after 72 hours of treatment with various concentrations of docetaxel or no pre-treatment with LGT-E.

Table 13 reports the results of an SRB cell viability assay of docetaxel-sensitive PC3 cells after 72 hours of treatment with various concentrations of LGT-E.

Table 14 reports the results of a sul-forhodamine B (SRB) cell viability assay of docetaxel-resistant PC3-TxR cells after 72 hours of treatment with various concentrations of LGT-E.

Table 15 reports the results of an SRB cell viability assay of docetaxel-resistant DU145-TxR cells after 72 hours of treatment with various concentrations of LGT-E.

Table 16 reports the results of a sul-forhodamine B (SRB) cell viability assay of docetaxel-sensitive DU145 cells after 72 hours of treatment with various concentrations of LGT-E.

Table 17 reports the cell lines and concentration ranges of four chemotherapeutic drugs that were used to establish the $IC_{50}$ for each drug.

Table 18 summarizes the results of the CE determinations for LGT-E in the contexts of docetaxel, daunorubicin, trastuzumab, and lapatinib.

Table 19 reports the results of a sul-forhodamine B (SRB) cell viability assay of docetaxel-sensitive DU145 cells that were pre-treated with 50 μg/ml LGT-E followed by 72 hours of treatment with various concentrations of docetaxel.

Table 20 reports the results of an SRB cell viability assay of docetaxel-docetaxel-sensitive DU145 cells after 72 hours of treatment with various concentrations of docetaxel and no pre-treatment with LGT-E.

Table 21 reports the results of a sul-forhodamine B (SRB) cell viability assay of Herceptin®-sensitive, HER2-positive breast ductal carcinoma line, BT474 cells that were pre-treated with 13 μg/ml LGT-E followed by 72 hours of treatment with various concentrations of Herceptin®.

Table 22 reports the results of a sul-forhodamine B (SRB) cell viability assay of Herceptin®-sensitive, HER2-positive breast ductal carcinoma line BT474, after 72 hours of treatment with various concentrations of Herceptin® and no pre-treatment with LGT-E.

Table 23 reports the results of a sul-forhodamine B (SRB) cell viability assay of Herceptin®-resistant, HER2-positive breast ductal carcinoma line, BT474/Her cells that were pre-treated with 13 μg/m LGT-E followed by 72 hours of treatment with various concentrations of Herceptin®.

Table 24 reports the results of a sul-forhodamine B (SRB) cell viability assay of Herceptin®-resistant, HER2-positive breast ductal carcinoma line BT474/Her, after 72 hours of treatment with various concentrations of Herceptin® and no pre-treatment with LGT-E.

Table 25 reports the results of a sul-forhodamine B (SRB) cell viability assay of Herceptin®-sensitive, HER2-positive breast ductal carcinoma line BT474, after 72 hours of treatment with various concentrations of lapatinib.

Table 26 reports the results of a sul-forhodamine B (SRB) cell viability assay of Herceptin®-resistant, HER2-positive breast ductal carcinoma line, BT474-TxR cells that were pre-treated with 13 μg/ml LGT-E followed by 72 hours of treatment with various concentrations of Herceptin®.

Table 27 reports the results of a sul-forhodamine B (SRB) cell viability assay of Herceptin®-resistant, HER2-positive breast ductal carcinoma line BT474-TxR, after 72 hours of treatment with various concentrations of Herceptin® and no pre-treatment with LGT-E.

Table 28 reports the results of an SRB cell viability assay of Herceptin®-resistant, HER2-positive breast ductal carcinoma BT474-TxR cells that were pre-treated with 12.5 μg/ml of LGT-E, followed by 72 hours of treatment with various concentrations of lapatinib.

Table 29 reports the results of an SRB cell viability assay of Herceptin®-resistant, HER2-positive breast ductal carcinoma BT474-TxR cells that were treated for 72 hours with various concentrations of lapatinib and no pre-treatment with LGT-E.

Table 30 reports the results of an SRB cell viability assay of Herceptin®-resistant, HER2-positive breast ductal carcinoma BT474-TxR cells that were pre-treated with 25 μg/ml of LGT-E, followed by 72 hours of treatment with various concentrations of lapatinib.

Table 31 reports the results of an SRB cell viability assay of Herceptin®-resistant, HER2-positive breast ductal carcinoma BT474-TxR cells that were treated for 72 hours with various concentrations of lapatinib and no pre-treatment with LGT-E.

Table 32 reports the results of an SRB cell viability assay of a lapatinib dose response analysis of lapatinib sensitivity in the lapatinib-senstive HER2-positive breast adenocarcinoma line.

Table 33 reports the results of an SRB cell viability assay of a lapatinib dose response analysis of lapatinib sensitivity in the lapatinib-resistant HER2-positive breast adenocarcinoma line.

Table 34 reports the results of an SRB cell viability assay of lapatinib-resistant HER2-positive breast adenocarcinoma SkBr3-TxR cells that were pre-treated with 12.5 μg/ml of LGT-E, followed by 72 hours of treatment with various concentrations of lapatinib.

Table 35 reports the results of an SRB cell viability assay of lapatinib-resistant HER2-positive breast adenocarcinoma SkBr3-TxR cells that were treated for 72 hours with various concentrations of lapatinib and no pre-treatment with LGT-E.

Table 36 reports the results of an SRB cell viability assay of daunorubicin-sensitive myelogenous leukemia K562 cells that were pre-treated with 25 μg/ml of LGT-E, followed by 72 hours of treatment with various concentrations of daunorubicin.

Table 37 reports the results of an SRB cell viability assay of daunorubicin-sensitive myelogenous leukemia K562 cells that were treated for 72 hours with various concentrations of daunorubicin and no pre-treatment with LGT-E.

Table 38 reports the results of an SRB cell viability assay of daunorubicin-resistant myelogenous leukemia K562/Dox cells that were pre-treated with 25 μg/ml of LGT-E, followed by 72 hours of treatment with various concentrations of daunorubicin.

Table 39 reports the results of an SRB cell viability assay of daunorubicin-resistant myelogenous leukemia K562/Dox cells that were treated for 72 hours with various concentrations of daunorubicin and no pre-treatment with LGT-E.

BRIEF DESCRIPTION OF THE DRAWINGS

FIG. 17 exemplifies the chemosensitizing effect of LGT-E in vivo.

DETAILED DESCRIPTION

Figure 1A:
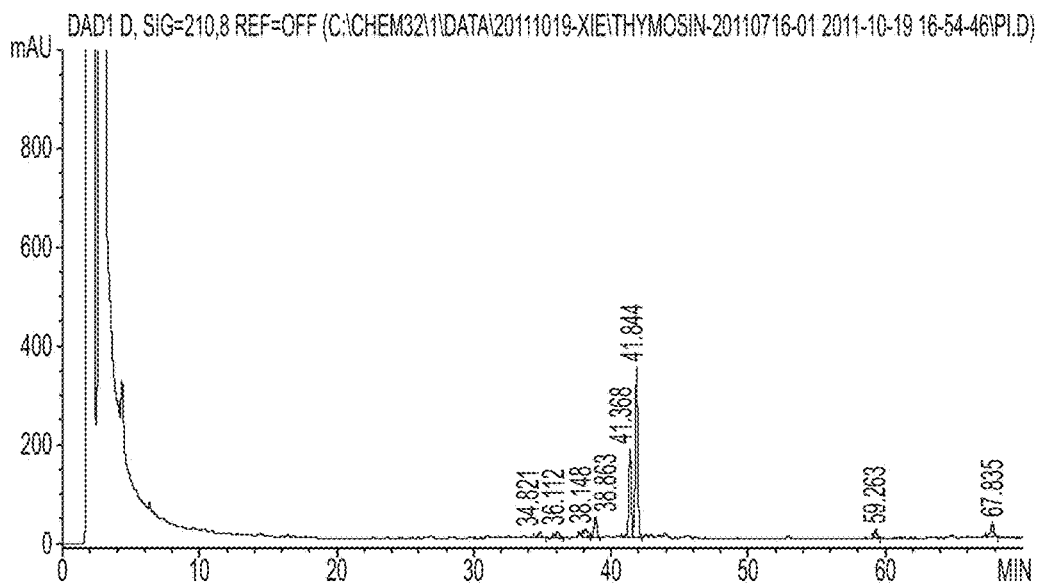
FIG. 1 shows the high pressure liquid chromatography-diode-array detection (HPLC-DAD) chromatograph finger prints for *T. Wilfordii* (A) root bark and (B) xylem tissue

Described herein are methods and pharmaceutical formulations for treating cancer by administering to a patient in need thereof, a combination of an ethanol extract of *T. wilfordii*, and a chemotherapeutic drug, wherein the ethanol extract of *T. wilfordii*, and the chemotherapeutic drug are administered in a combined amount effective to treat the cancer. In various embodiments, methods of the invention treat cancer that is at least in part resistant to treatment by a chemotherapeutic drug when the chemotherapeutic drug is administered alone, i.e., in the absence of the ethanol extract of *T. wilfordii*. Therefore, in various embodiments, the methods of the invention overcome anti-cancer chemotherapeutic drug resistance by contacting a chemotherapeutic drug-resistant cancerous cell with at least one component of the ethanol extraction of *T. Wilfordii*, as described herein, and effect a reversal of the cell's resistance to chemotherapeutic drug, thereby allowing the chemotherapeutic drug to cause the drug-resistant cancerous cell's death or cytostasis. Thus, the methods of treatment of the invention are used to inhibit, retard or prevent growth of tumor cells that are resistant to a chemotherapeutic agent.

The *T. wilfordii* extracts of the invention are obtained from the root xylem of *Tripterygium wilfordii* Hook f., a medicinal plant that was obtained from the Province of Jilin, China. As stated above, the methods of the invention use an ethanol extraction of *T. Wilfordii*. In various embodiments, the methods of the invention use an ethanol extract of *T. Wilfordii* that was prepared by combining extracted material from serial 95% ethanol extractions. In various other embodiments, ethanol-extracted *T. Wilfordii* material is further extracted by adsorbing the extracted material to a silica gel, and subjecting the adsorbed material to additional ethanol extractions. The ethanol is typically removed from extractions by subjecting the extractions to rotary evaporation. The dried material may optionally be freeze dried. The final, dried ethanol extract of *T. wilfordii* that is used by the method is termed LGT-E, and is characterized by having the liquid chromatography and mass spectrometry chromatogram that is described in FIG. 2.

Cancers that can be treated by the methods of the invention include both solid and haematological tumurs of various organs. Nonlimiting examples of solid tumors are metastatic breast cancer, and prostate cancer, including androgen-dependent and androgen-independent prostate cancer. Haematolgical tumors that are treatable by the methods of the invention include, for example, chronic myelogenous leukemia (CML), which is characterized by abnormal proliferation of immature granulocytes, for example, neutrophils, eosinophils and basophils, in the blood, bone marrow, the spleen, liver and sometimes in other tissues.

Non-limiting examples of chemotherapeutic drugs suitable for use in combination with the extracts or extract components of T. Wilfordii of the invention include: topoisomerase inhibitors, including, e.g., doxorubicin and daunorubicin; taxanes, including docetaxel; and biologics that target receptors that are embedded in the surface of targeted cells, for example the HER receptors, including HER2/neu, which is the target of trastuzumab (sold under the Herceptin® brandname).

As used herein, the term "treating" or "treatment" refers to coadministering an ethanol extract of T. wilfordii with a chemotherapeutic drug to a subject that has cancer that is resistant to treatment with the chemotherapeutic drug, with the purpose to cure, heal, alleviate, relieve, alter, remedy, ameliorate, improve, or affect cancer. In various embodiments, the method of the invention administers the ethanol extract of T. Wilfordii of the invention and the chemotherapeutic drug that is co-administered with the extract at the same time or in immediate succession, while in other embodiments, the ethanol extract of T. Wilfordii is administered prior to the administration of the chemotherapeutic drug to allow the cells of the cancer that is being treated to become at least partially sensitized prior to being contacted with the chemotherapeutic drug.

The term "an effective amount" refers to the amount of the ethanol extract of T. wilfordii that is required to confer a reduction in the resistance of the cancer cells to a designated chemotherapeutic drug. Effective amounts may vary, as recognized by those skilled in the art, depending on route of administration, excipient usage, and the possibility of co-usage with other agents.

As stated above, the invention includes pharmaceutical compositions that comprise the extracts or extracted components of T. Wilfordii. To practice the method of this invention, the aforementioned pharmaceutical compositions can be administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques.

Injectable compositions can be prepared in conventional forms, either as liquid solutions or suspensions, solid forms suitable for solution or suspension in liquid prior to injection, or as emulsions. The injectables, solutions and emulsions may also contain one or more excipients. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

A composition for oral administration can be any orally acceptable dosage form including, but not limited to, capsules, tablets, emulsions and aqueous suspensions, dispersions and solutions. In the case of tablets for oral use, carriers that are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents.

The carrier in the pharmaceutical composition must be "acceptable" in the sense of being compatible with the active ingredient of the formulation (and preferably, capable of stabilizing it) and not deleterious to the subject to be treated. For example, one or more solubilizing agents, which form more soluble complexes with the fused bicyclic or tricyclic compounds, or more solubilizing agents, can be utilized as pharmaceutical carriers for delivery of the active compounds. Examples of other carriers include colloidal silicon dioxide, magnesium stearate, sodium lauryl sulfate, and D&C Yellow #10.

EXAMPLES

Example 1

Figure 1B:
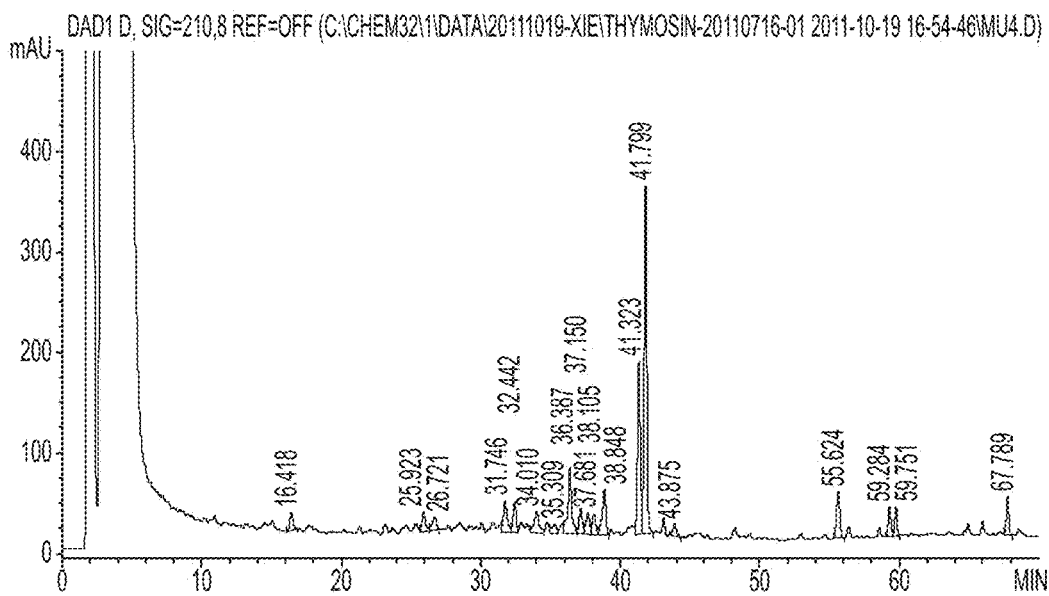

Authentication of Tripterygium wilfordii Hook.f. T. wilfordii roots were purchased from Sanyuan Pharmaceuticals Co. Ltd. (Jilin, Peoples Republic of China) and authentified at the Macau Institute of Applied Researchfor Medicine and Health of Macau University of Science and Technology, Macau, as follows. T. wilfordii root bark and root xylem were authenticated according to the same protocol. Thus, root bark and root xylem tissue, were each ground to a powder and passed through a 60 mesh sieve. For each root or xylem preparation, 0.2 g of the ground powder was precisely weighed and 20 mL of ethyl acetate was added. The sample was extracted using bath sonication for 1 hour at 45° C. The mix was filtered, and the residue was resuspended using 20 mL of methanol, followed by bath sonication for another 1 hour at 45° C. The ethyl acetate extract and methanol extracts were combined and evaporated to dryness using a rotary evaporator. The solid extract was reconstituted using 2 ml of methanol and filtered through a 0.45 µg filter. The HPLC-DAS High pressure liquid chromatography (HPLC) chromatography was performed with an Agilent 1200 Series LC System and Modules (Agilent Technologies, Santa Clara, Calif.). Chromatography was carried out using a Symmetry C18 (250×4.6 mm, 5 µm) column (Waters Corp., Milford, Mass.). The temperature of analytical column was set at 20° C., and the detection wave length was 210 nm. A linear gradient elution was carried out using a mobile phase containing acetonitrile (A) and 0.1% phosphoric acid (v/v) (B) with the flow rate of 1 ml/min. The gradient began with 40% eluent A and 60% eluent B. The gradient was changed linearly to 50% eluent B in 20 min, 25% eluent B in 20 min, and 20% eluent B in 10 min. The gradient was then further changed back to 80% of eluent B in 10 min and kept at this percentage. The HPLC-diode-array detection (HPLC-DAD) chromatograph finger prints for T. Wilfordii root bark and xylem tissue are shown in FIGS. 1A and 1B, respectively.

Preparation of *T. Wilfordii* Extract.

*T. Wilfordii* root xylem tissue (390.61 g) was placed into a blender and blended into small pieces. The blended root material was added to 2 L of 95% ethanol, sonicated for one hour, and then macerated overnight in the 95% ethanol overnight. Afterwards, the material was pressured filtered using a vacuum, and the ethanol was collected. The residue that remained after pressure filtering was washed twice with 600 mL of 95% ethanol, and sonicated for 30 minutes with each wash cycle. The ethanol from the two washes was combined with initial 2 L of ethanol, and the combined extractions were evaporated using a rotating evaporator, and then freeze dried. The total yield of the foregoing extraction procedure yielded 16.16 g of ethanol-extracted material, which was further fractionated by adsorbing the evaporated product on silica gel 60 and subjecting the adsorbed material to sequential extractions in the following order of solvents: 95% ethanol and chloroform. The chemosensitizing effect of the ethanol and chloroform extracts were quantitated. An aqueous extract was also prepared and its CE was determined to compare with the ethanol and choloroform extracts. The *T. Wilfordii* aqueous extract was sourced from Yunnan, China, and was obtained from Jiangyin Tianjiang Pharmaceutical Co., Ltd. (Jiangsu, China), and is commercially available through ACE Pharmaceuticals Ltd. (Hong Kong).

Assessing Chemosensitivity of Extracts

A chemosensitizing effect (CE) is a measure of the degree to which a compound can lower, (i.e., chemosensitize), the required concentration of a chemotherapeutic drug's half maximal inhibitory concentration ($IC_{50}$) when the compound and the chemotherapeutic drug are coadministered. Here, $IC_{50}$ is the concentration of a chemotherapeutic drug that inhibits cell proliferation by 50%. The CE is expressed as: $CE=IC_{50D}/IC_{50E+D}$. $IC_{50D}$ is the $IC_{50}$ of the chemotherapeutic drug against which an test extract (or other compound suspected of having a CE) is evaluated. $IC_{50E+D}$ is the $IC_{50}$ of the combination of the test extract and chemotherapeutic drug. The CE of a test extract or compound can vary depending on the type of cell and the specific chemotherapeutic or class or combination of therapeutics that are being evaluated.

Frequently, a test extract or compound may also be non-specifically cytotoxic (as opposed to a chemotherapeutic drug that targets tumor cells) when it is administered at concentrations greater than that required to produce a CE. Ideally, the concentration of test compound that is required to produce a CE is significantly lower than its $IC_{50}$. The variance between those concentrations can be quantitated by calculating the Chemosensitizing Utility Index (CUI) value for a test extract or compound. The CUI is expressed as: $CUI=CE \times (IC_{50E}/Con_E)$. $IC_{50E}$ is the concentration of an extract, e.g., an extract or extracted compound of *Tripterygium wilfordii*, that inhibits cell proliferation by 50%. $Con_E$ is the concentration of an extract or compound that is required to produce desirable CE. Extracts and compounds that are found to have desirable CE and CUI values are then tested for their potential as chemosensitizing agents in an in vivo context.

CE and CUI values were obtained individually for the aqueous, ethanol, and chloroform extracts that are described above. These analyses were performed using the chemotherapeutic, docetaxel, in conjuntion with docetaxel-resistant prostate cancer line, PC3-TxR (University of Michigan), using the sulforhodamine B (SRB)-based proliferation assay that is described in Example 5, below. All of the foregoing extracts were associated with desireable CE and CUI values. The $IC_{50E+D}$ concentrations of the aqueous, ethanol, and chloroform extracts were 9.3, 3.97, and 3.8 nM, respectively, and the CUI values were 17.74, 27.39, and 17.37, respectively. Based on its relatively high CUI value, the ethanol was selected for further study, as chronicled in the Examples, below. In the Examples, the ethanol, is referred to as Lei Gong Teng extract (LGT-E).

Liquid chromatography and mass spectrometry (LC-MS) analysis of LGT-E. A 500 mg/ml stock solution of the LGT-E extract product, prepared as described above, was made by dissolving 500 mg of LGT-E extract in ethanol. The stock was further diluted to 500 μg/ml in 80% acetonitrile. An aliquot of 10 μl was used for LC-MS/MS analysis using an API 3200 LC/MS/MS system (Applied Biosystems, Foster City, Calif., USA) and two Shimadzu LC-20AD Prominence Liquid Chromatograph pumps equipped with an SIL-20A Prominence autosampler (Shimadzu, Columbia, Md., USA). Chromatography was carried out using a Zorbax SB C18 column (150×2.1 mm, 5 μm, Zorbax, Agilent, Santa Clara, Calif., USA) which was proceeded with a SB-C18 Guard Cartridges (12.5×2.1 mm, Zorbax, Agilent, Santa Clara, Calif., USA).

Figure 2:
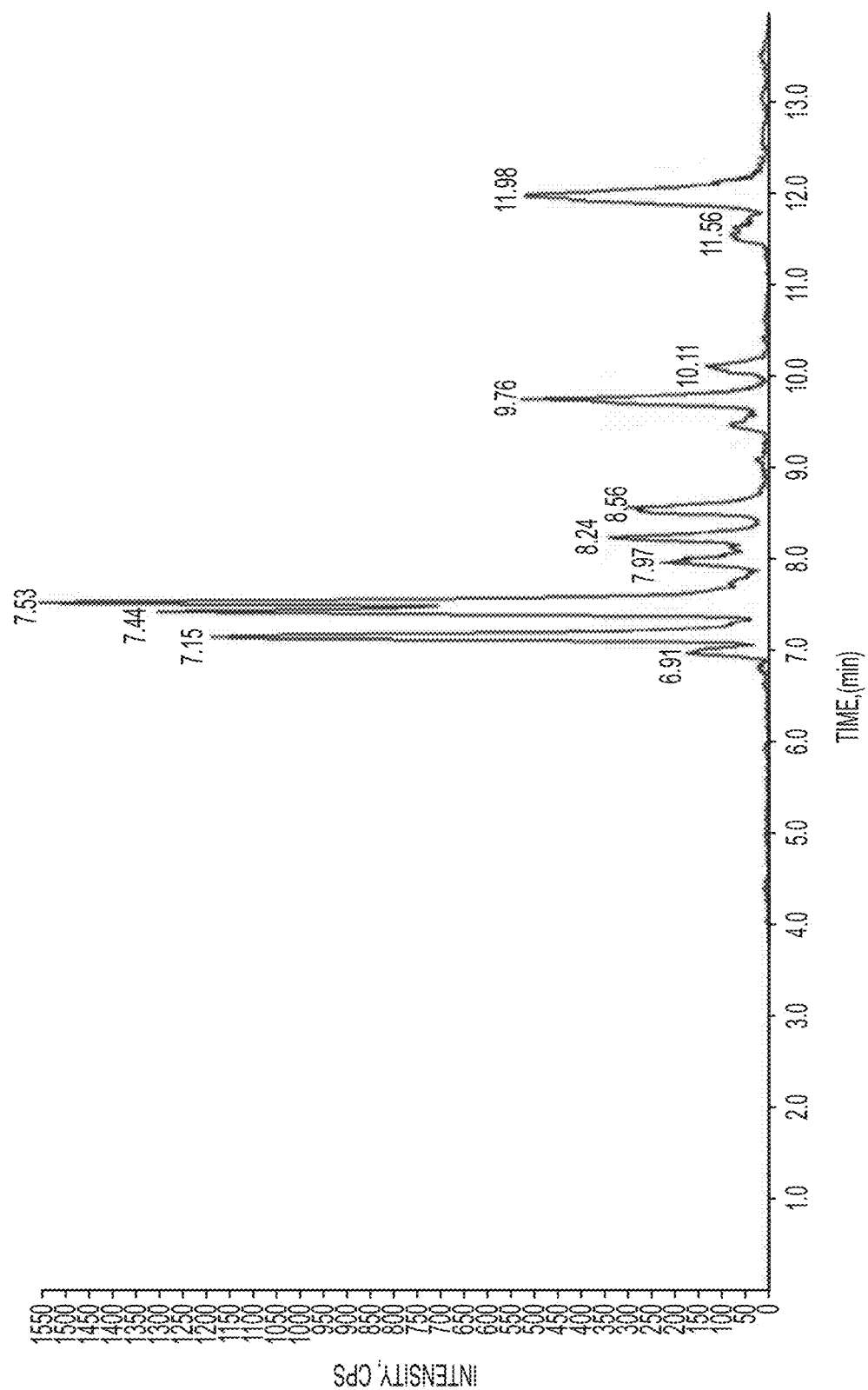
FIG. 2 shows the liquid chromatography and mass spectrometry chromatogram for the *T. Wilfordii* extract product, Lei Gong Teng extract (LGT-E).

A linear gradient elution was carried out using a mobile phase containing acetonitrile (A) and 0.2% formic acid containing 2 mM ammonia acetate (B) with the flow rate of 0.35 ml/min. The gradient began with 30% eluent A and 70% eluent B for 3 min and was changed linearly to 40% eluent B in 2 min and remained for 2 min. The gradient was then changed back to 95% eluent B in 1 min and kept at this percentage for 6 min. The temperatures of analytical column and autosampler were both set at room temperature. All the liquid chromatographic eluent was then introduced into the atmospheric-pressure chemical ionization (APCI) source. Mass spectrometric conditions were: gas 1, nitrogen (30 psi); gas 2, nitrogen (30 psi); nebulizer current (5.0 v); source temperature, 400° C.; curtain gas, nitrogen (25 psi). The HPLC chromatogram for LGT-E is shown in FIG. 2.

Cell lines used to assess the CE of LGT-E. The continued analyses of the chemosensitizing effect of LGT-E that is described in the Examples, herein, utilized the following human cell lines: (i) The docetaxel-resistant prostate cancer lines, DU145-TxR and PC3-TxR (Provided by Department of Medicine, University of Pittsburgh and Partners Healthcare, but the PC3-TxR cells used in Examples 2-7 were obtained from the University of Michigan); (ii) The docetaxel-sensitive lines, PC3 and DU145 (Purchased from ATCC, Manassas, Va., USA); (iii) The Herceptin®-sensitive, HER2-positive breast ductal carcinoma line, BT474 (Provided by Dr. Cui, Cedars-Sinai, Beverly Hills, Calif.); (iv) the Herceptin®-resistant, HER2-positive breast adenocarcinoma line, SkBr3 (Provided by Dr. Xiaojiang Cui, Cedars-Sinai, Beverly Hills, Calif.); and (v) The doxorubicin-sensitive and -resistant myelogenous leukemia lines K562 and K562/Dox, respectively (Provided by Dr. Kenneth Chan, Ohio State University).

Example 2

Dosage-Dependent Effect of LGT-E on the Sensitization of the Docetaxel-Resistant Prostate Cancer Cell Line, PC3-TrX, to Docetaxel.

PC3-TxR cells were plated into sterile, F-bottom Cellstar® 96 well cell culture plates with lids (Cat #655180, Purchased from Greiner Bio-one, Monroe, N.C.) by placing into each well, 100 μl of medium containing 3000 cells in RPMI 1640 supplemented with 10% fetal bovine serum (Thermo Scientific, Logan, Utah) and a solution of penicillin (100 U/ml) and streptomycin (100 μg/ml) (Life Technologies Grand Island, N.Y.). The cells were at passage 52 at the time of plating. Triplicate wells were assigned to each experimental condition tested, and a 24 hour recovery period for the cells following the seeding of the wells was allowed. During the recovery period, the cells were incubated at 37° C. and 5% $CO_2$.

The LGT-E was prepared by adding an appropriate amount of LGT-E powder to DMSO to form a 500 mg/ml stock solution. The stock solution was alternately vortexed and sonicated until the LGT-E powder went into solution. The stock solution was diluted in RPMI 1640 medium (Mediatech, Manassas, Va., or Life Technologies Grand Island, NY) to reach the desired concentrations of LGT-E (e.g., 12, 25, or 60 μg/ml).

Pretreatment of the cells with LGT-E was carried out by aspirating the media from the wells, followed by adding 50 μl of LGT-E solution containing concentrations of either 12 or 25 μg/ml of LGT-E solution and incubation of the cells for two hours under conditions of 37° C. and 5% $CO_2$. At the end of the two hour pre-treatment period, 1:3 serially-diluted, 50 μl aliquots of docetaxel that contained from $1\times10^2$ to $1\times10^{-3}$ nM of docetaxel in RPMI 1640 medium (i.e., 100, 33.3, 10.0, 3.33, 1.0, 0.333, 0.1, and 0.001 nM) were added to the pretreated cells in the presence of the LGT-E media. The docetaxel was diluted from a stock solution (105 μM docetaxel in DMSO, Cat #: 01885, purchased from Sigma-Aldrich, St. Louis, Mo.) immediately before being added to the cells. After adding docetaxel, the cells were incubated for an additional 72 hours under the same temperature and atmospheric conditions used for the pre-treatment step.

Following the 72 hour docetaxel treatment period, the the sulforhodamine B (SRB) assay was used to quantitate living cells. Media was aspirated from each well, and replaced with a 10% solution of cold trichloroacetic acid (TCA) (Cat #: T6399, purchased from Sigma-Aldrich), and incubated for one hour at 4° C. After the TCA incubation, the TCA solution was aspirated, and the cells were washed five times with tap water. After removing the last wash, the plates were left with lids off at room temperature until the surfaces were dry, which took one to two hours. Then 50 μl of a 0.4% solution of sul-forhodamine B (SRB) sodium salt (Cat #: S9012, purchased from Sigma-Aldrich) was added to each well and the plates were incubated at room temperature for 20 to 30 minutes. Afterwards, the wells were washed five times with a 1% acetic acid solution in 10 mM TRIS base (Cat#: 161-0719, purchased from Bio-Rad Laboratories, Hercules, Calif.). The plates were subsequently left to dry for several hours or overnight. SRB that remained in the dried wells was solubilized by adding 100 μl of SRB solubilization solution (10 mM TRIS base) to each well, and placing the plates either on a gently-moving shaker or letting the plates remain stationary at room temperature until the SRB dissolves, which takes about five to ten minutes. The amount of SRB in each well, which correlated directly to the number of living cells at fixation, was determined spectrophotometrically at an absorbance of 565 nm by a microplate reader. Increases or decreases in cell viability were determined by comparing LGT-E pretreated cells with cells that had also been treated with docetaxel, but were not treated with LGT-E.

Figure 3A:
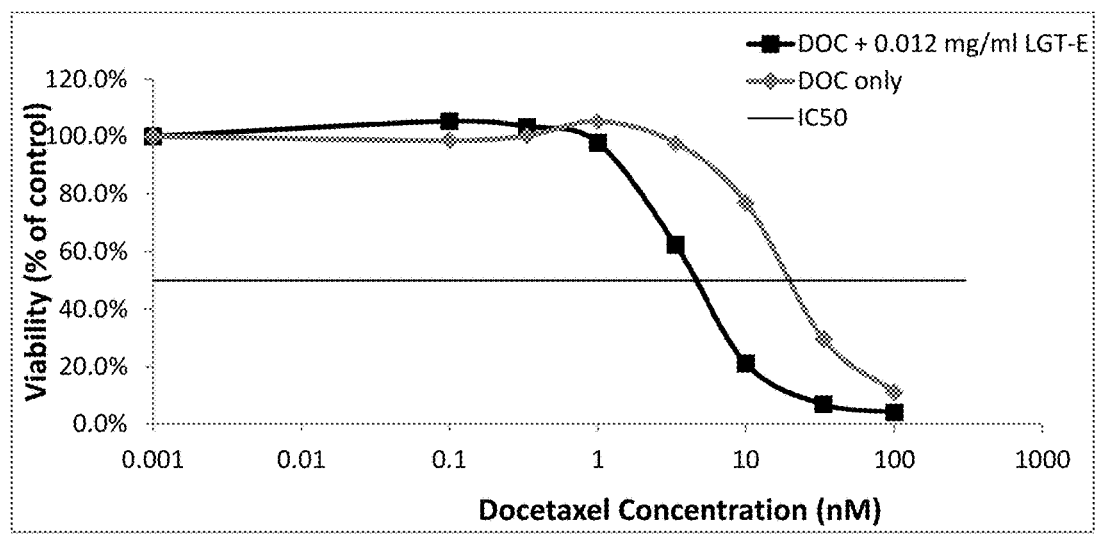
FIG. 3 shows sulforhodamine B (SRB) cell viability assay results from docetaxel-resistant PC3-TxR cells that were pre-treated with (A) 12 μg/ml of Lei Gong Teng extract (LGT-E) or (B) 25 μg/ml of LGT-E followed by 72 hours of treatment with various concentrations of docetaxel. See Tables 1-4.
Figure 3B:
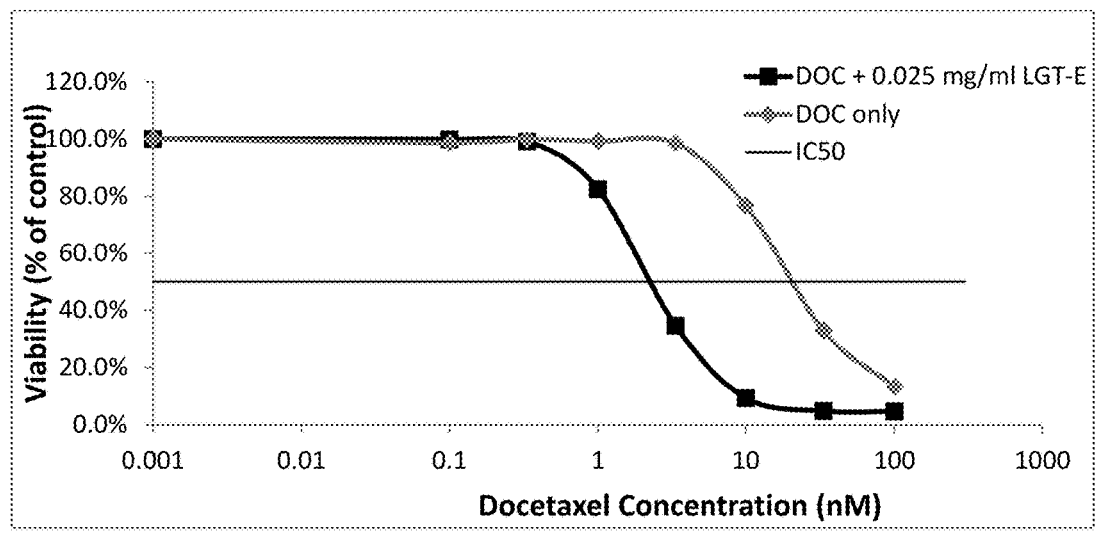

The results for the experiments that are described in this Example are as follows: Tables 1 and 3 report the cell viability data relating to pre-treatment with 12 and 25 μg/ml LGT-E; Tables 2 and 4 report control data obtained by treating the cells with only the assigned concentrations of docetaxel. FIG. 3 summarizes the data of Tables 1-4 in graphical form.

TABLE 1

| Docetaxel (nM) | 100 | 33.3 | 10 | 3.33 | 1 | 0.333 | 0.1 | 0.001 |
|---|---|---|---|---|---|---|---|---|
| A at 565 nm | 0.090 | 0.140 | 0.422 | 1.275 | 1.924 | 2.084 | 2.091 | 2.084 |
| (in triplicate) | 0.077 | 0.143 | 0.460 | 1.329 | 2.011 | 2.124 | 2.125 | 2.074 |
| background = 0.047 | 0.084 | 0.145 | 0.418 | 1.225 | 2.066 | 2.140 | 2.249 | 1.979 |
| mean A | 0.084 | 0.143 | 0.433 | 1.276 | 2.000 | 2.116 | 2.155 | 2.046 |
| SD | 0.007 | 0.003 | 0.023 | 0.052 | 0.072 | 0.029 | 0.083 | 0.058 |
| % viable | 4.1 | 7.0 | 21.2 | 62.4 | 97.8 | 103.4 | 105.3 | 100.0 |
| CV | 7.79 | 1.77 | 5.35 | 4.08 | 3.58 | 1.36 | 3.86 | 2.83 |

TABLE 2

| Docetaxel (nM) | 100 | 33.3 | 10 | 3.33 | 1 | 0.333 | 0.1 | 0.001 |
|---|---|---|---|---|---|---|---|---|
| A at 565 nm | 0.243 | 0.672 | 1.716 | 2.124 | 2.316 | 2.142 | 2.190 | 2.257 |
| (in triplicate) | 0.257 | 0.699 | 1.734 | 2.195 | 2.337 | 2.354 | 2.216 | 2.185 |
| background = 0.047 | 0.252 | 0.605 | 1.676 | 2.184 | 2.354 | 2.173 | 2.151 | 2.215 |
| mean A | 0.251 | 0.659 | 1.709 | 2.168 | 2.336 | 2.223 | 2.186 | 2.219 |
| SD | 0.007 | 0.048 | 0.030 | 0.038 | 0.019 | 0.115 | 0.033 | 0.036 |
| % viable | 11.3 | 29.7 | 77.0 | 97.7 | 105.3 | 100.2 | 98.5 | 100.0 |
| CV | 2.83 | 7.35 | 1.74 | 1.76 | 0.82 | 5.15 | 1.50 | 1.63 |

TABLE 3

| Docetaxel (nM) | 100 | 33.3 | 10 | 3.33 | 1 | 0.333 | 0.1 | 0.001 |
|---|---|---|---|---|---|---|---|---|
| A at 565 nm | 0.092 | 0.104 | 0.200 | 0.754 | 1.672 | 2.013 | 2.071 | 2.027 |
| (in triplicate) | 0.115 | 0.102 | 0.203 | 0.699 | 1.774 | 2.104 | 2.122 | 2.066 |

TABLE 3-continued

| Docetaxel (nM) | 100 | 33.3 | 10 | 3.33 | 1 | 0.333 | 0.1 | 0.001 |
|---|---|---|---|---|---|---|---|---|
| background = 0.047 | 0.085 | 0.095 | 0.179 | 0.681 | 1.634 | 1.991 | 1.960 | 2.068 |
| mean A | 0.097 | 0.100 | 0.194 | 0.711 | 1.693 | 2.036 | 2.051 | 2.053 |
| SD | 0.016 | 0.005 | 0.013 | 0.038 | 0.072 | 0.060 | 0.083 | 0.023 |
| % viable | 4.7 | 4.9 | 9.4 | 34.6 | 82.5 | 99.1 | 99.9 | 100.0 |
| CV | 16.19 | 4.73 | 6.76 | 5.35 | 4.28 | 2.94 | 4.04 | 1.13 |

TABLE 4

| Docetaxel (nM) | 100 | 33.3 | 10 | 3.33 | 1 | 0.333 | 0.1 | 0.001 |
|---|---|---|---|---|---|---|---|---|
| A at 565 nm | 0.332 | 0.763 | 1.791 | 2.350 | 2.432 | 2.413 | 2.363 | 2.449 |
| (in triplicate) | 0.306 | 0.776 | 1.862 | 2.321 | 2.369 | 2.373 | 2.292 | 2.376 |
| background = 0.047 | 0.313 | 0.801 | 1.802 | 2.332 | 2.255 | 2.314 | 2.360 | 2.285 |
| mean A | 0.317 | 0.780 | 1.818 | 2.334 | 2.352 | 2.366 | 2.338 | 2.370 |
| SD | 0.013 | 0.019 | 0.038 | 0.015 | 0.090 | 0.050 | 0.040 | 0.082 |
| % viable | 13.4 | 32.9 | 76.7 | 98.5 | 99.2 | 99.9 | 98.7 | 100.0 |
| CV | 4.25 | 2.48 | 2.10 | 0.63 | 3.82 | 2.10 | 1.72 | 3.47 |

Example 3

Dosage-Dependent Effect of LGT-E on the Sensitization of the Docetaxel-Resistant Prostate Cancer Cell Line, DU145-TrX, to Docetaxel.

Figure 4A:
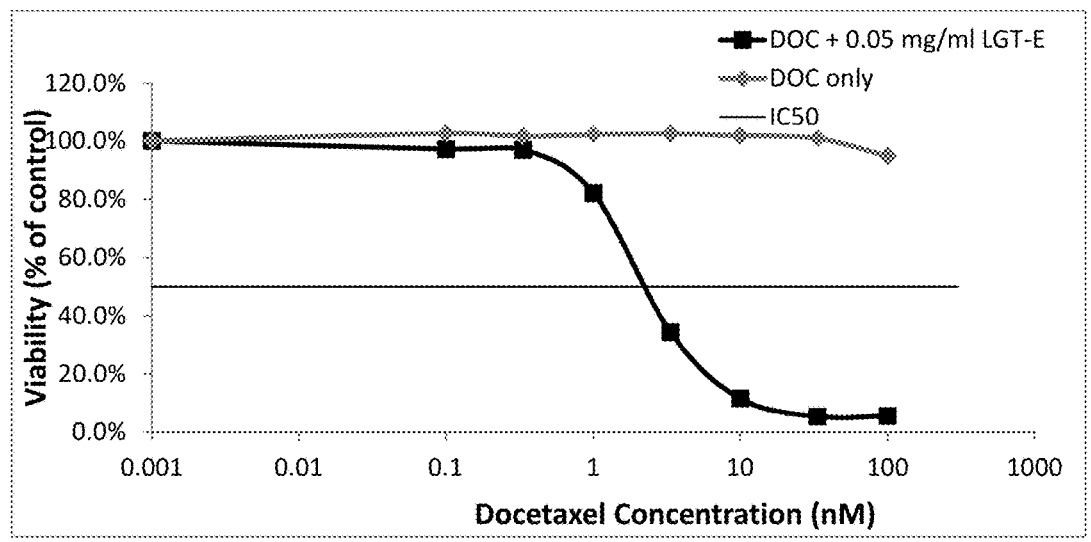
FIG. 4 shows sulforhodamine B (SRB) cell viability assay results from docetaxel-resistant DU145-TxR cells that were pre-treated with (A) 50 μg/ml of LGT-E, (B) 25 μg/ml of LGT-E, or (C) 12.5 μg/ml of LGT-E followed by 72 hours of treatment with various concentrations of docetaxel. See Tables 5-10.
Figure 4B:
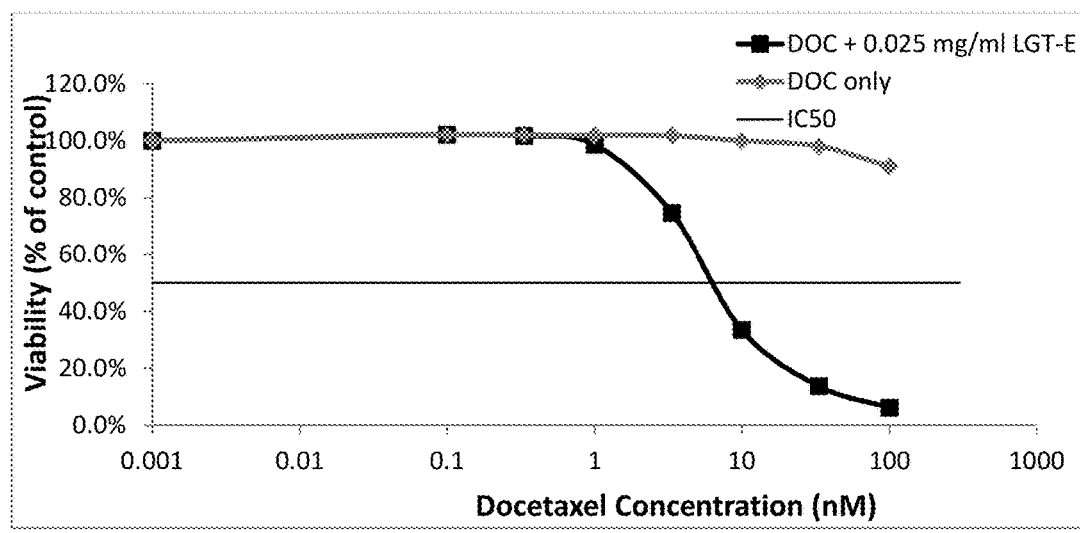
Figure 4C:
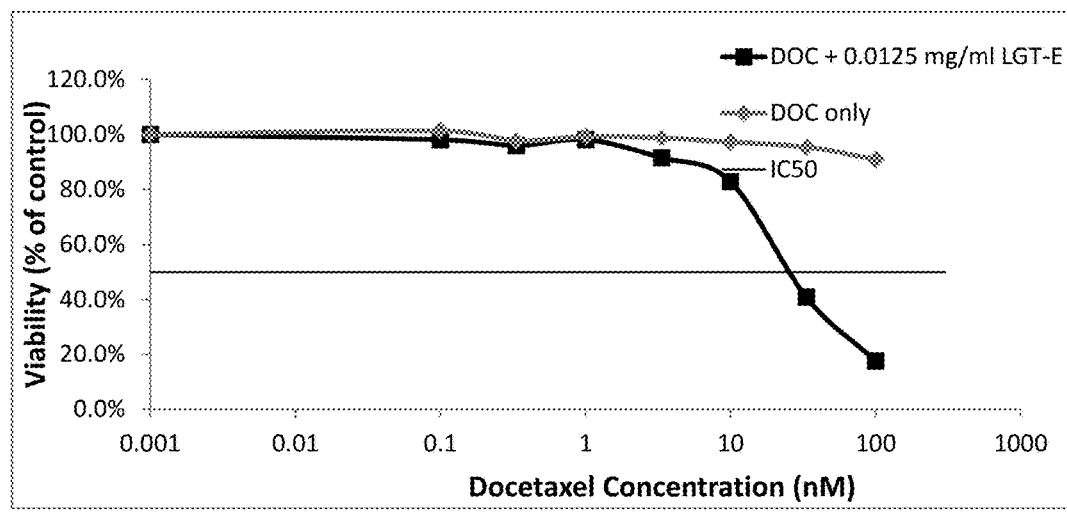

Using the methods described in Example 2, the chemosensitizing effect of LGT-E pretreatment on docetaxel-treated DU145-TrX cells was studied. In this study, cells were pre-treated with either 50, 25, or 12.5 µg/ml of LGT-E before treating the cells with 1:3 serially-diluted, 50 µl aliquots of docetaxel that contained from $1\times10^2$ to $1\times10$ nM of docetaxel. The DU145-TxR cells were plated at passage 38. Tables 5, 7 and 9 report the cell viability data relating to pre-treatment with 50, 25, and 12.5 µg/ml LGT-E, respectively. Tables 6, 8, and 10 report control data obtained from DU145-TxR cells that were not pre-treated with LGT-E. FIG. 4 summarizes the data of Tables 5-10 in a graphical format.

TABLE 5

| Docetaxel (nM) | 100 | 33.3 | 10 | 3.33 | 1 | 0.333 | 0.1 | 0.001 |
|---|---|---|---|---|---|---|---|---|
| A at 565 nm | 0.110 | 0.103 | 0.260 | 0.638 | 1.565 | 1.846 | 1.854 | 1.922 |
| (in triplicate) | 0.103 | 0.103 | 0.214 | 0.679 | 1.576 | 1.978 | 1.989 | 1.985 |
| background = 0.046 | 0.118 | 0.115 | 0.222 | 0.741 | 1.770 | 1.978 | 1.974 | 2.076 |
| mean A | 0.110 | 0.107 | 0.232 | 0.686 | 1.637 | 1.934 | 1.939 | 1.994 |
| SD | 0.008 | 0.007 | 0.025 | 0.052 | 0.115 | 0.076 | 0.074 | 0.077 |
| % viable | 5.5 | 5.4 | 11.6 | 34.4 | 82.1 | 97.0 | 97.2 | 100.0 |
| CV | 6.81 | 6.48 | 10.60 | 7.56 | 7.04 | 3.94 | 3.82 | 3.88 |

TABLE 6

| DU145-TxR cells, no pre-treatment | | | | | | | | |
|---|---|---|---|---|---|---|---|---|
| Docetaxel (nM) | 100 | 33.3 | 10 | 3.33 | 1 | 0.333 | 0.1 | 0.001 |
| A at 565 nm | 2.268 | 2.368 | 2.380 | 2.399 | 2.385 | 2.360 | 2.441 | 2.408 |
| (in triplicate) | 2.159 | 2.369 | 2.397 | 2.434 | 2.398 | 2.414 | 2.379 | 2.309 |
| background = 0.046 | 2.192 | 2.304 | 2.332 | 2.316 | 2.350 | 2.318 | 2.338 | 2.262 |
| mean A | 2.206 | 2.347 | 2.370 | 2.383 | 2.378 | 2.364 | 2.386 | 2.326 |
| SD | 0.056 | 0.037 | 0.034 | 0.061 | 0.025 | 0.048 | 0.052 | 0.075 |
| % viable | 94.8 | 100.9 | 101.9 | 102.4 | 102.2 | 101.6 | 102.6 | 100.0 |
| CV | 2.53 | 1.59 | 1.42 | 2.54 | 1.04 | 2.04 | 2.17 | 3.20 |

TABLE 7

| Docetaxel (nM) | 100 | 33.3 | 10 | 3.33 | 1 | 0.333 | 0.1 | 0.001 |
|---|---|---|---|---|---|---|---|---|
| A at 565 nm | 0.139 | 0.337 | 0.762 | 1.752 | 2.312 | 2.349 | 2.437 | 2.379 |
| (in triplicate) | 0.142 | 0.332 | 0.825 | 1.863 | 2.385 | 2.534 | 2.377 | 2.359 |
| background = 0.046 | 0.158 | 0.305 | 0.786 | 1.681 | 2.298 | 2.334 | 2.432 | 2.354 |

TABLE 7-continued

| Docetaxel (nM) | 100 | 33.3 | 10 | 3.33 | 1 | 0.333 | 0.1 | 0.001 |
|---|---|---|---|---|---|---|---|---|
| mean A | 0.147 | 0.325 | 0.791 | 1.766 | 2.332 | 2.406 | 2.416 | 2.364 |
| SD | 0.010 | 0.017 | 0.032 | 0.092 | 0.047 | 0.111 | 0.033 | 0.013 |
| % viable | 6.2 | 13.7 | 33.5 | 74.7 | 98.6 | 101.8 | 102.2 | 100.0 |
| CV | 6.96 | 5.30 | 4.02 | 5.20 | 2.00 | 4.63 | 1.38 | 0.56 |

TABLE 8

| Docetaxel (nM) | 100 | 33.3 | 10 | 3.33 | 1 | 0.333 | 0.1 | 0.001 |
|---|---|---|---|---|---|---|---|---|
| A at 565 nm | 2.185 | 2.349 | 2.450 | 2.494 | 2.430 | 2.525 | 2.531 | 2.492 |
| (in triplicate) | 2.194 | 2.371 | 2.444 | 2.450 | 2.438 | 2.453 | 2.449 | 2.369 |
| background = 0.046 | 2.136 | 2.302 | 2.269 | 2.342 | 2.428 | 2.323 | 2.327 | 2.297 |
| mean A | 2.172 | 2.341 | 2.388 | 2.429 | 2.432 | 2.434 | 2.436 | 2.386 |
| SD | 0.031 | 0.035 | 0.103 | 0.078 | 0.005 | 0.102 | 0.103 | 0.099 |
| % viable | 91.0 | 98.1 | 100.1 | 101.8 | 101.9 | 102.0 | 102.1 | 100.0 |
| CV | 1.44 | 1.51 | 4.31 | 3.22 | 0.22 | 4.21 | 4.21 | 4.13 |

TABLE 9

| Docetaxel (nM) | 100 | 33.3 | 10 | 3.33 | 1 | 0.333 | 0.1 | 0.001 |
|---|---|---|---|---|---|---|---|---|
| A at 565 nm | 0.420 | 1.055 | 2.116 | 2.412 | 2.562 | 2.451 | 2.538 | 2.562 |
| (in triplicate) | 0.408 | 1.059 | 2.152 | 2.385 | 2.479 | 2.538 | 2.540 | 2.650 |
| background = 0.046 | 0.542 | 1.090 | 2.219 | 2.365 | 2.635 | 2.522 | 2.596 | 2.612 |
| mean A | 0.457 | 1.068 | 2.163 | 2.388 | 2.559 | 2.504 | 2.558 | 2.608 |
| SD | 0.074 | 0.019 | 0.052 | 0.024 | 0.078 | 0.046 | 0.033 | 0.044 |
| % viable | 17.5 | 41.0 | 82.9 | 91.5 | 98.1 | 96.0 | 98.1 | 100.0 |
| CV | 16.22 | 1.79 | 2.42 | 0.99 | 3.05 | 1.85 | 1.29 | 1.69 |

TABLE 10

DU145-TxR cells, no pre-treatment

| Docetaxel (nM) | 100 | 33.3 | 10 | 3.33 | 1 | 0.333 | 0.1 | 0.001 |
|---|---|---|---|---|---|---|---|---|
| A at 565 nm | 2.342 | 2.416 | 2.402 | 2.480 | 2.513 | 2.454 | 2.600 | 2.538 |
| (in triplicate) | 2.274 | 2.395 | 2.508 | 2.511 | 2.551 | 2.494 | 2.600 | 2.515 |
| background = 0.046 | 2.196 | 2.338 | 2.372 | 2.409 | 2.372 | 2.372 | 2.391 | 2.439 |
| mean A | 2.271 | 2.383 | 2.428 | 2.467 | 2.479 | 2.440 | 2.531 | 2.498 |
| SD | 0.073 | 0.040 | 0.071 | 0.052 | 0.094 | 0.062 | 0.121 | 0.052 |
| % viable | 90.9 | 95.4 | 97.2 | 98.8 | 99.3 | 97.7 | 101.3 | 100.0 |
| CV | 3.22 | 1.69 | 2.94 | 2.12 | 3.80 | 2.55 | 4.77 | 2.07 |

Example 4

A Comparison of the Docetaxel Sensitivity of Docetaxel-Sensitive Prostate Cancer Cells to that of Docetaxel-Resistant Prostate Cancer Cells.

Figure 5:
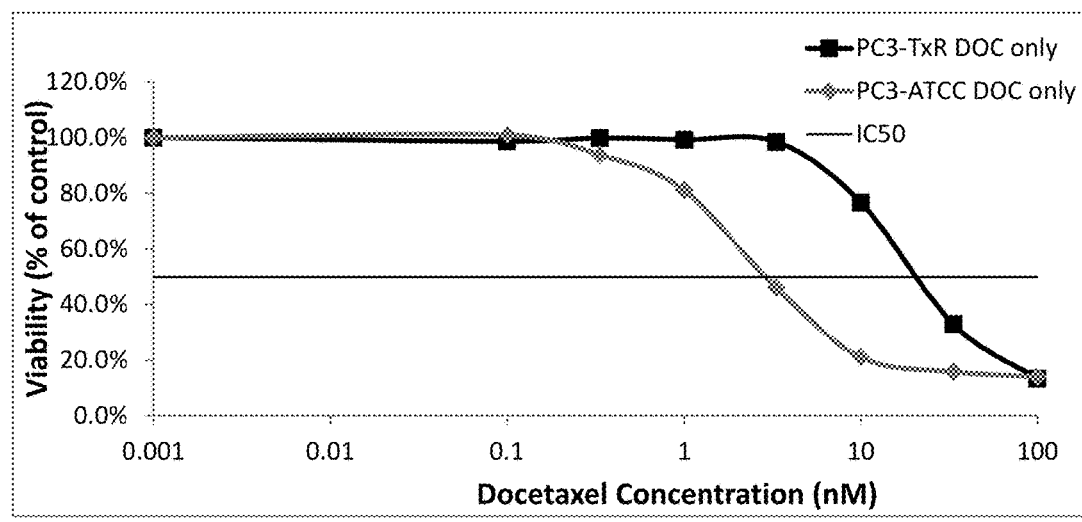
FIG. 5 shows sulforhodamine B (SRB) cell viability assay results from a docetaxel dose-response analysis of (A) docetaxel-resistant PC3-TxR cells and (B) docetaxel-sensitive PC3 cells. See Tables 11 and 12.

To determine the degree to which the docetaxel-resistant cell lines were more resistant to docetaxel than their respective parental docetaxel-sensitive cell lines, cell viabilities of the docetaxel-resistant PC3-TxR cell line and the docetaxel-sensitive cell line from which PC3-TxR was derived, PC3, were compared following docetaxel treatment in the absence of LGT-E pre-treatment. Cell culture conditions, docetaxel treatment, and cell viability analysis were performed as described in Example 2. As in Example 2, cells were treated with 1:3 serially-diluted, 50 µl aliquots of docetaxel that contained from $1 \times 10^2$ to $1 \times 10^{-3}$ nM of docetaxel. The PC3-TrX and PC3 cells were plated at passages 52 and 11, respectively. Tables 11 and 12 show the data obtained from docetaxel treatment of docetaxel-resistant PC3-TxR cells, and docetaxel-sensitive PC3 cells, respectively. FIG. 5 summarizes the data of Tables 11 and 12 in a graphical format.

TABLE 11

| Docetaxel (nM) | 100 | 33.3 | 10 | 3.33 | 1 | 0.333 | 0.1 | 0.001 |
|---|---|---|---|---|---|---|---|---|
| A at 565 nm | 0.332 | 0.763 | 1.791 | 2.350 | 2.432 | 2.413 | 2.363 | 2.449 |
| (in triplicate) | 0.306 | 0.776 | 1.862 | 2.321 | 2.369 | 2.373 | 2.292 | 2.376 |
| background = 0.049 | 0.313 | 0.801 | 1.802 | 2.332 | 2.255 | 2.314 | 2.360 | 2.285 |
| mean A | 0.317 | 0.780 | 1.818 | 2.334 | 2.352 | 2.366 | 2.338 | 2.370 |
| SD | 0.013 | 0.019 | 0.038 | 0.015 | 0.090 | 0.050 | 0.040 | 0.082 |
| % viable | 13.4 | 32.9 | 76.7 | 98.5 | 99.2 | 99.9 | 98.7 | 100.0 |
| CV | 4.25 | 2.48 | 2.10 | 0.63 | 3.82 | 2.10 | 1.72 | 3.47 |

TABLE 12

| Docetaxel (nM) | 100 | 33.3 | 10 | 3.33 | 1 | 0.333 | 0.1 | 0.001 |
|---|---|---|---|---|---|---|---|---|
| A at 565 nm | 0.287 | 0.354 | 0.448 | 1.038 | 1.811 | 1.982 | 2.591 | 2.362 |
| (in triplicate) | 0.331 | 0.370 | 0.450 | 1.090 | 1.855 | 2.247 | 2.097 | 2.291 |
| background = 0.049 | 0.330 | 0.339 | 0.517 | 0.976 | 1.797 | 2.091 | 2.111 | 2.082 |
| mean A | 0.316 | 0.354 | 0.472 | 1.035 | 1.821 | 2.107 | 2.266 | 2.245 |
| SD | 0.025 | 0.016 | 0.039 | 0.057 | 0.030 | 0.133 | 0.281 | 0.146 |
| % viable | 14.1 | 15.8 | 21.0 | 46.1 | 81.1 | 93.8 | 101.0 | 100.0 |
| CV | 7.95 | 4.38 | 8.33 | 5.52 | 1.66 | 6.32 | 12.41 | 6.48 |

Example 5

Determination of the LGT-E $IC_{50}$ for Docetaxel-Sensitive and Docetaxel-Resistant Prostate Cancer Cells.

Figure 6A:
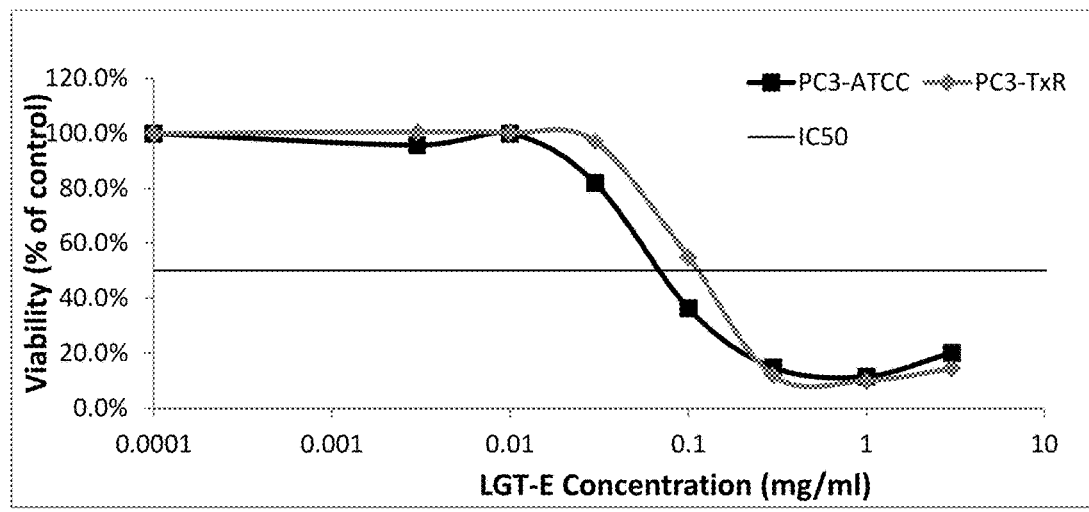
FIG. 6 shows sulforhodamine B (SRB) cell viability assay results from a LGT-E dose-response analysis of (A) docetaxel-sensitive PC3 and docetaxel-resistant PC3-TxR cells and (B) docetaxel-sensitive DU145 cells and docetaxel-resistant DU145-TxR cells. See Tables 13-16.
Figure 6B:
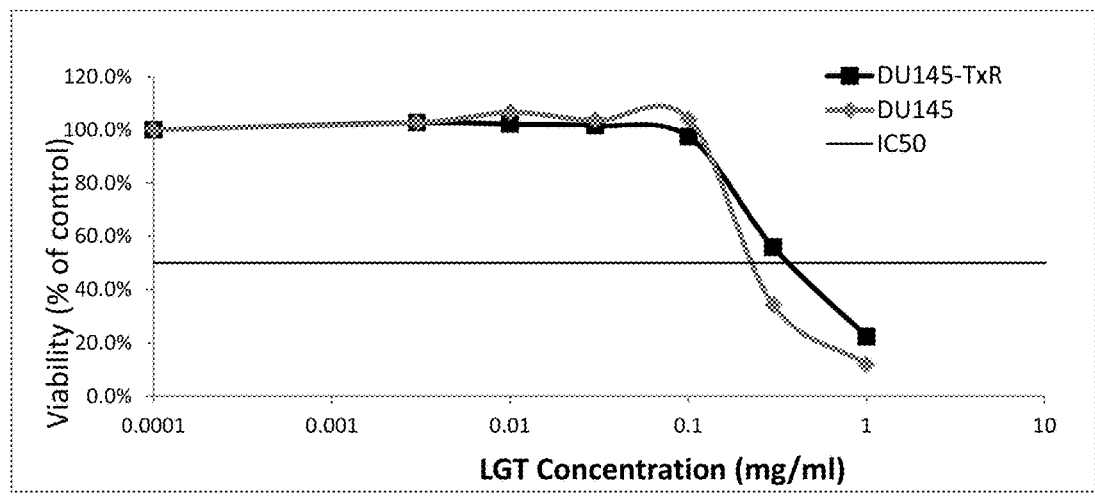

LGT-E $IC_{50}$ concentrations were determined for the docetaxel-sensitive cell lines, PC3 and DU145, as well as for their docetaxel-resistant sub-lines. Cell culture conditions and cell viability analysis were performed as described in Example 2. Unlike in Example 2, however, the cells were subjected to a 72 hour incubation under standard culture conditions in the presence of either 100.0, 33.3, 10.0, 3.33, 1.0, 0.333, 0.1, or 0.001 µg/ml of LGT-E, and the cells were not treated with docetaxel. PC3 and PC3-TrX cells were plated at passages 15 and 38, respectively, and DU145 and DU145-TrX cells were each plated at passage 46. Tables 13 and 14 report cell viability data that was obtained from PC3 and PC3-TxR cells, respectively. Tables 15 and 16 report cell viability data that was obtained from DU145-Txr and DU145 cells, respectively. FIG. 6 summarizes the data of Tables 13-16 in a graphical format.

TABLE 13

| LGT-E (µg/ml) | 100 | 33.3 | 10 | 3.33 | 1 | 0.333 | 0.1 | 0.001 |
|---|---|---|---|---|---|---|---|---|
| A at 565 nm | 0.355 | 0.208 | 0.255 | 0.665 | 1.327 | 1.649 | 1.555 | 1.629 |
| (in triplicate) | 0.328 | 0.186 | 0.250 | 0.560 | 1.496 | 1.723 | 1.658 | 1.705 |
| background = 0.046 | 0.323 | 0.181 | 0.235 | 0.590 | 1.281 | 1.629 | 1.579 | 1.668 |
| mean A | 0.335 | 0.192 | 0.247 | 0.605 | 1.368 | 1.667 | 1.597 | 1.667 |
| SD | 0.017 | 0.014 | 0.010 | 0.054 | 0.113 | 0.050 | 0.054 | 0.038 |
| % viable | 20.1 | 11.5 | 14.8 | 36.3 | 82.0 | 100.0 | 95.8 | 100.0 |
| CV | 5.13 | 7.49 | 4.22 | 8.94 | 8.27 | 2.97 | 3.37 | 2.28 |

TABLE 14

| LGT-E (µg/ml) | 100 | 33.3 | 10 | 3.33 | 1 | 0.333 | 0.1 | 0.001 |
|---|---|---|---|---|---|---|---|---|
| A at 565 nm | 0.354 | 0.245 | 0.279 | 1.261 | 2.395 | 2.416 | 2.468 | 2.455 |
| (in triplicate) | 0.366 | 0.260 | 0.311 | 1.503 | 2.445 | 2.559 | 2.536 | 2.495 |
| background = 0.046 | 0.353 | 0.241 | 0.291 | 1.331 | 2.394 | 2.508 | 2.497 | 2.506 |
| mean A | 0.358 | 0.249 | 0.294 | 1.365 | 2.411 | 2.494 | 2.500 | 2.485 |
| SD | 0.007 | 0.010 | 0.016 | 0.125 | 0.029 | 0.072 | 0.034 | 0.027 |
| % viable | 14.4 | 10.0 | 11.8 | 54.9 | 97.0 | 100.4 | 100.6 | 100.0 |
| CV | 2.02 | 4.03 | 5.50 | 9.12 | 1.21 | 2.91 | 1.36 | 1.08 |

TABLE 15

| LGT-E (µg/ml) | 100 | 33.3 | 10 | 3.33 | 1 | 0.333 | 0.1 | 0.001 |
|---|---|---|---|---|---|---|---|---|
| A at 565 nm | 1.247 | 0.442 | 1.224 | 1.883 | 1.966 | 1.936 | 1.953 | 1.880 |
| (in triplicate) | 1.699 | 0.416 | 1.156 | 1.948 | 1.995 | 1.999 | 2.056 | 2.034 |
| background = 0.043 | 1.173 | 0.444 | 0.869 | 1.827 | 1.940 | 2.002 | 1.962 | 1.896 |
| mean A | 1.373 | 0.434 | 1.083 | 1.886 | 1.967 | 1.979 | 1.990 | 1.936 |
| SD | 0.285 | 0.016 | 0.188 | 0.061 | 0.028 | 0.037 | 0.057 | 0.085 |
| % viable | 70.9 | 22.4 | 55.9 | 97.4 | 101.6 | 102.2 | 102.8 | 100.0 |
| CV | 0.207 | 0.036 | 0.174 | 0.032 | 0.014 | 0.019 | 0.029 | 0.044 |

TABLE 16

| LGT-E (µg/ml) | 100 | 33.3 | 10 | 3.33 | 1 | 0.333 | 0.1 | 0.001 |
|---|---|---|---|---|---|---|---|---|
| A at 565 nm | 1.036 | 0.217 | 0.651 | 2.179 | 2.162 | 2.235 | 2.163 | 2.109 |
| (in triplicate) | 1.104 | 0.257 | 0.685 | 2.148 | 2.174 | 2.229 | 2.097 | 2.090 |
| background = 0.043 | 0.854 | 0.272 | 0.792 | 2.129 | 2.083 | 2.150 | 2.115 | 2.002 |
| mean A | 0.998 | 0.248 | 0.709 | 2.152 | 2.139 | 2.204 | 2.125 | 2.067 |
| SD | 0.129 | 0.028 | 0.074 | 0.025 | 0.049 | 0.047 | 0.034 | 0.057 |
| % viable | 48.3 | 12.0 | 34.3 | 104.1 | 103.5 | 106.7 | 102.8 | 100.0 |
| CV | 0.130 | 0.115 | 0.104 | 0.012 | 0.023 | 0.022 | 0.016 | 0.028 |

Example 6

Comparison of CE Values for LGT-E when Paired with Various Different Chemotherapeutic Drugs and Carcinoma Cell Lines.

In this comparison, the LGT-E $IC_{50}$ was determined for: (i) Docetaxel paired with the docetaxel-sensitive cell lines, PC3 and DU145, as well as for their docetaxel-resistant sub-lines; (ii) Doxorubicin paired with the doxorubicin-sensitive and -resistant myelogenous leukemia lines K562 and K562/Dox, respectively; (iii) The Herceptin®-sensitive, HER2-positive breast ductal carcinoma line, BT474; and (iv) The Herceptin®-resistant, HER2-positive breast adenocarcinoma line, SkBr3. Cell culture of the above cell lines was performed as described in Example 2, except that 5,000, rather than 3,000 cells were plated per well for the K562, K562/Dox, BT474, SkBr3 lines.

The chemotherapeutic drugs that were tested for chemosensitization in combination with LTG-E were docetaxel, daunorubicin, Herceptin®, and lapatinib. To determine $IC_{50}$ for each of those drugs, as well as verify the known drug sensitivities of the cell lines used in these studies, cell lines were plated as detailed above, and cultured in the presence of the aforementioned chemotherapeutic drugs, as shown in Table 17, for 72 hours, followed by SRB analysis of cell viabilities. Table 17 also contains the serially-diluted concentrations of drugs that each cell line was tested against.

TABLE 17

| Chemotherapeutic Drug | Range of Drug Concentrations used to determine $IC_{50}$ | Cell Line used to determine $IC_{50}$ |
| --- | --- | --- |
| Docetaxel | 100, 33, 10, 3.3, 1, 0.3, 0.1 (nM) | PC3 and DU145 |
| Herceptin ® | 30, 10, 3, 1, 0.3, 0.1, 0.03 (µM) | BT474 |
| Lapatinib | 20, 6.7, 2, 0.7, 0.2, 0.07, 0.02 (µM) | BT474 and SkBr3 |
| Daunorubicin | 100, 33, 10, 3.3, 1, 0.3, 0.1 (µM) | K562 |

After the $IC_{50}$ concentrations were determined for docetaxel, daunorubicin, Herceptin®, and lapatinib, CE values for the drugs was determined by pre-treating cultures of the chemotherapeutic drug-resistant cell lines that had been prepared, plated, and viabilities assayed as described in Examples 2 and 4, with either LGT-E at 12.5, 25 and 50 µg/ml. As in Example 2, the pre-treatment period was two hours. Table 18 summarizes the results of the CE determinations for the chemotherapeutic drugs.

TABLE 18

| Therapeutic Drug | Sensitizing Agent (µg/ml) | | Cell Line | $IC_{50}$ of drug when cells treated with drug only | $IC_{50}$ of drug when cells pre-treated with Chemosensitizing Agent before drug treatment | CE |
| --- | --- | --- | --- | --- | --- | --- |
| docetaxel | none added | | PC3 | 1.796 nM (1.45 ng/ml) | | |
| | LGT-E | 12.5 | PC3-TxR | 17.54 nM (14.17 ng/ml) | 4.077 nM (3.29 ng/ml) | 4.3 |
| | LGT-E | 25 | PC3-TxR | 18.33 nM (14.8 ng/ml) | 2.195 nM (1.77 ng/ml) | 8.35 |
| | LGT-E | 50 | DU-145 | 6.652 nM (5.37 ng/ml) | 3.389 nM (2.74 ng/ml) | |
| | LGT-E | 12.5 | DU-145-TxR | >100 nM (80.78 ng/ml) | 23.49 nM (18.98 ng/ml) | 4.26 |
| | LGT-E | 25 | DU-145-TxR | >100 nM (80.78 ng/ml) | 5.759 nM (4.65 ng/ml) | >17.36 |
| daunorubicin | none added | | K562 | 1.046 µM (0.55 µg/ml) | | |
| | LGT-E | 25 | K562 | 32.62 µM (17.2 µg/ml) | 6.534 µM (3.45 µg/ml) | 4.99 |
| Herceptin ® | none added | | BT474 | 3.593 µM (523 µg/ml) | | |
| | LGT-E | 12.5 | BT474-TxR | 30 µM (4366 µg/ml) | 30 µM (4366 µg/ml) | 1.0 |
| lapatinib | none added | | BT474 | 0.1158 µM (0.067 µg/ml) | | |
| | LGT-E | 12.5 | BT474-TxR | 20 µM (11.6 µg/ml) | 4 µM (2.32 µg/ml) | 5.0 |
| | LGT-E | 25 | BT474-TxR | 11 µM (6.39 µg/ml) | 2 µM (1.16 µg/ml) | 5.5 |
| | none added | | SkBr3 | 0.2407 µM (0.14 µg/ml) | | |
| | LGT-E | 12.5 | SkBr3-TxR | 6.204 µM (3.6 µg/ml) | 3.924 µM (2.28 µg/ml) | 1.58 |

Example 7

Dosage-Dependent Effect of LGT-E on the Sensitization of the Docetaxel-Sensitive Prostate Cancer Cell Line, DU145, to Docetaxel.

Figure 7:
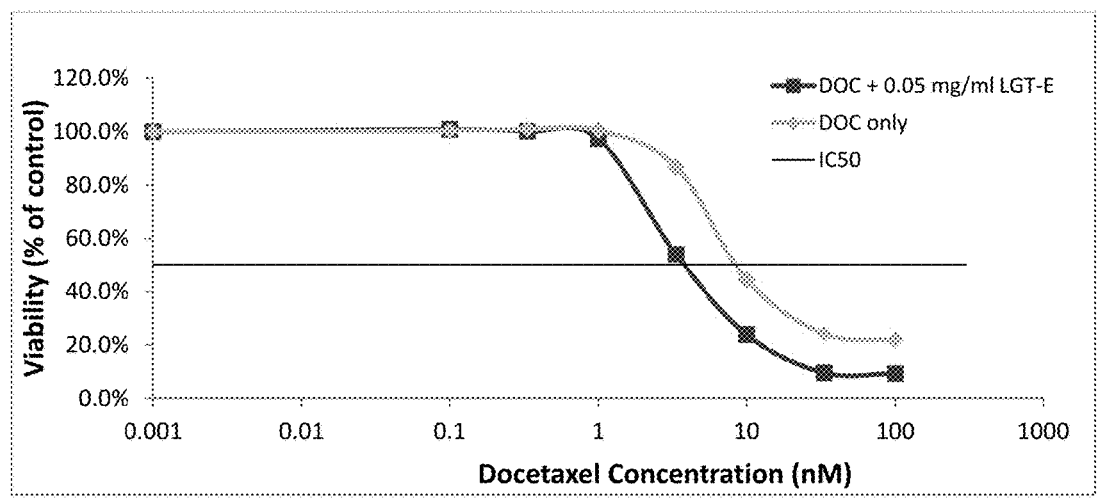
FIG. 7 shows sulforhodamine B (SRB) cell viability assay results from a docetaxel dose-response analysis of docetaxel-sensitive DU145 cells that were pretreated with 50 μg/ml of LGT-E See Tables 19-20.

Using the methods described in Example 2, the chemosensitizing effect of LGT-E pretreatment on docetaxel-treated DU145 cells was studied. In this study, cells were pre-treated with 50 µg/ml of LGT-E before treating the cells with 1:3 serially-diluted, 50 µl aliquots of docetaxel that contained from $1 \times 10^2$ to $1 \times 10^{-3}$ nM of docetaxel. Table 19 reports the cell viability data. Table 20 reports control data obtained from DU145 cells that were not pre-treated with LGT-E. FIG. 7 summarizes the data of Tables 19 and 20 in a graphical format.

TABLE 19

| Docetaxel (nM) | 100 | 33.3 | 10 | 3.33 | 1 | 0.333 | 0.1 | 0.001 |
| --- | --- | --- | --- | --- | --- | --- | --- | --- |
| A at 565 nm | 0.220 | 0.241 | 0.620 | 1.407 | 2.574 | 2.685 | 2.633 | 2.652 |
| (in triplicate) | 0.265 | 0.283 | 0.610 | 1.437 | 2.561 | 2.581 | 2.703 | 2.662 |
| background = 0.060 | 0.247 | 0.229 | 0.656 | 1.416 | 2.551 | 2.645 | 2.628 | 2.581 |
| mean A | 0.244 | 0.251 | 0.629 | 1.420 | 2.562 | 2.637 | 2.655 | 2.632 |
| SD | 0.023 | 0.028 | 0.024 | 0.015 | 0.012 | 0.052 | 0.042 | 0.044 |
| % viable | 9.3 | 9.6 | 23.9 | 54.0 | 97.4 | 100.2 | 100.9 | 100.0 |
| CV | 9.27 | 11.28 | 3.85 | 1.08 | 0.45 | 1.99 | 1.58 | 1.68 |

TABLE 20

| Docetaxel (nM) | 100 | 33.3 | 10 | 3.33 | 1 | 0.333 | 0.1 | 0.001 |
|---|---|---|---|---|---|---|---|---|
| A at 565 nm | 0.589 | 0.694 | 1.184 | 2.318 | 2.758 | 2.769 | 2.740 | 2.741 |
| (in triplicate) | 0.650 | 0.635 | 1.268 | 2.365 | 2.741 | 2.760 | 2.733 | 2.730 |
| background = 0.060 | 0.555 | 0.652 | 1.196 | 2.453 | 2.756 | 2.771 | 2.775 | 2.744 |
| mean A | 0.598 | 0.661 | 1.216 | 2.379 | 2.752 | 2.767 | 2.750 | 2.739 |
| SD | 0.048 | 0.030 | 0.045 | 0.069 | 0.009 | 0.006 | 0.023 | 0.007 |
| % viable | 21.8 | 24.1 | 44.4 | 86.9 | 100.5 | 101.0 | 100.4 | 100.0 |
| CV | 8.04 | 4.60 | 3.73 | 2.88 | 0.34 | 0.21 | 0.82 | 0.27 |

Example 8

Figure 8:
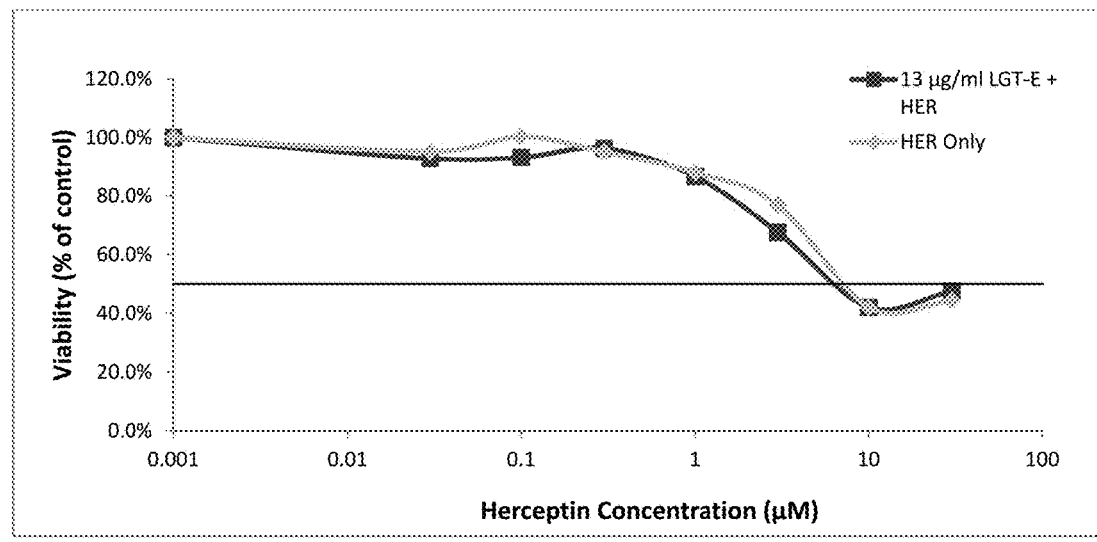
FIG. 8 shows sulforhodamine B (SRB) cell viability assay results from a Herceptin® dose-response analysis of Herceptin®-sensitive, HER2-positive breast ductal carcinoma line, BT474 that were pretreated with 13 μg/ml of LGT-E See Tables 21-22.

Limited additional Herceptin® sensitization provided by LTG-E pre-treatment of Herceptin®-sensitive, HER2-positive breast ductal carcinoma line, BT474. Using the cell culture methods described in Examples 2 and 9, as adapted for Herceptin® treatment of BT474 cells, the chemosensitizing effect of LTG-E pretreatment on Herceptin®-treated BT474 cells was studied. In this study, cells were pre-treated with 13 µg/ml of LTG-E before treating the cells with 1:3 serially-diluted, 50 µl aliquots of Herceptin® that contained from $1\times10^2$ to $1\times10^{-3}$ µM of Herceptin®. Table 21 reports the cell viability data relating to pre-treatment with LTG-E prior to Herceptin® treatment. Table 22 reports control data obtained from cells that were not pre-treated with LTG-E prior to Herceptin® treatment. FIG. 8 summarizes the data of Tables 21 and 22 in a graphical format.

TABLE 21

| Trastuzumab (µM) | 30 | 10 | 3 | 1 | 0.3 | 0.1 | 0.03 | 0.001 |
|---|---|---|---|---|---|---|---|---|
| A at 565 nm | 0.607 | 0.416 | 0.970 | 1.247 | 1.441 | 1.431 | 1.491 | 1.541 |
| (in triplicate) | 0.693 | 0.708 | 0.959 | 1.321 | 1.417 | 1.328 | 1.323 | 1.423 |
| background = 0.045 | 0.760 | 0.696 | 0.997 | 1.182 | 1.315 | 1.277 | 1.204 | 1.367 |
| mean A | 0.687 | 0.607 | 0.976 | 1.250 | 1.391 | 1.346 | 1.340 | 1.444 |
| SD | 0.077 | 0.165 | 0.020 | 0.070 | 0.067 | 0.078 | 0.144 | 0.089 |
| % viable | 47.6 | 42.0 | 67.6 | 86.6 | 96.4 | 93.2 | 92.8 | 100.0 |
| CV | 11.16 | 27.21 | 2.00 | 5.56 | 4.81 | 5.83 | 10.76 | 6.15 |

TABLE 22

| Trastuzumab (µM) | 30 | 10 | 3 | 1 | 0.3 | 0.1 | 0.03 | 0.001 |
|---|---|---|---|---|---|---|---|---|
| A at 565 nm | 0.815 | 0.717 | 1.187 | 1.386 | 1.490 | 1.508 | 1.405 | 1.596 |
| (in triplicate) | 0.565 | 0.648 | 1.225 | 1.462 | 1.581 | 1.669 | 1.678 | 1.690 |
| background = 0.045 | 0.759 | 0.657 | 1.293 | 1.389 | 1.512 | 1.660 | 1.505 | 1.533 |
| mean A | 0.713 | 0.674 | 1.235 | 1.413 | 1.528 | 1.613 | 1.530 | 1.607 |
| SD | 0.131 | 0.038 | 0.054 | 0.043 | 0.047 | 0.090 | 0.138 | 0.079 |
| % viable | 44.4 | 42.0 | 76.9 | 87.9 | 95.1 | 100.4 | 95.2 | 100.0 |
| CV | 18.39 | 5.56 | 4.35 | 3.05 | 3.11 | 5.61 | 9.03 | 4.92 |

Example 9

LGT-E-Mediated Herceptin® Sensitization Provided by LTG-E Pre-Treatment of Herceptin®-Resistant, HER2-Positive Breast Ductal Carcinoma Line, BT474/her.

Figure 9:
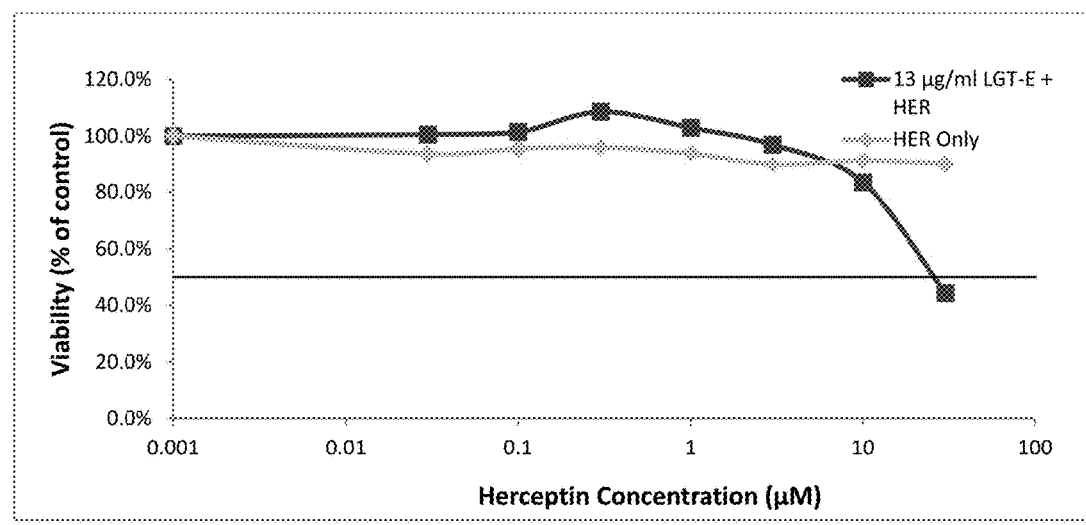
FIG. 9 shows sulforhodamine B (SRB) cell viability assay results from a Herceptin® dose-response analysis of Herceptin®-resistant, HER2-positive breast ductal carcinoma line, BT474/Her that were pretreated with 13 μg/ml of LGT-E See Tables 23-24.

Using the cell culture methods described in Examples 2 and 9, as adapted for Herceptin® treatment of BT474 cells, the chemosensitizing effect of LTG-E pretreatment on Herceptin®-treated BT474/Her cells was studied. In this study, cells were pre-treated with 13 µg/ml of LTG-E before treating the cells with 1:3 serially-diluted, 50 µl aliquots of Herceptin® that contained from $1\times10^2$ to $1\times10^{-3}$ µM of Herceptin®. Table 23 reports the cell viability data relating to pre-treatment with LTG-E prior to Herceptin® treatment. Table 24 reports control data obtained from cells that were not pre-treated with LTG-E prior to Herceptin® treatment. FIG. 9 summarizes the data of Tables 23 and 24 in a graphical format.

TABLE 23

| Trastuzumab (µM) | 30 | 10 | 3 | 1 | 0.3 | 0.1 | 0.03 | 0.001 |
|---|---|---|---|---|---|---|---|---|
| A at 565 nm | 1.020 | 1.755 | 1.757 | 1.928 | 1.947 | 1.808 | 1.780 | 1.792 |
| (in triplicate) | 0.803 | 1.638 | 1.599 | 1.713 | 1.837 | 1.665 | 1.689 | 1.682 |
| background = 0.047 | 0.468 | 0.920 | 1.655 | 1.680 | 1.829 | 1.772 | 1.729 | 1.695 |

TABLE 23-continued

| Trastuzumab (µM) | 30 | 10 | 3 | 1 | 0.3 | 0.1 | 0.03 | 0.001 |
|---|---|---|---|---|---|---|---|---|
| mean A | 0.764 | 1.438 | 1.670 | 1.774 | 1.871 | 1.748 | 1.733 | 1.723 |
| SD | 0.278 | 0.452 | 0.080 | 0.135 | 0.066 | 0.074 | 0.046 | 0.060 |
| % viable | 44.3 | 83.4 | 96.9 | 102.9 | 108.6 | 101.5 | 100.6 | 100.0 |
| CV | 36.41 | 31.45 | 4.80 | 7.59 | 3.52 | 4.25 | 2.63 | 3.49 |

TABLE 24

| Trastuzumab (µM) | 30 | 10 | 3 | 1 | 0.3 | 0.1 | 0.03 | 0.001 |
|---|---|---|---|---|---|---|---|---|
| A at 565 nm | 1.870 | 1.758 | 1.867 | 2.128 | 2.104 | 2.137 | 2.016 | 2.238 |
| (in triplicate) | 2.271 | 2.417 | 2.299 | 2.271 | 2.327 | 2.323 | 2.346 | 2.432 |
| background = 0.047 | 2.216 | 2.254 | 2.172 | 2.216 | 2.346 | 2.279 | 2.249 | 2.386 |
| mean A | 2.119 | 2.143 | 2.113 | 2.205 | 2.259 | 2.246 | 2.204 | 2.352 |
| SD | 0.217 | 0.343 | 0.222 | 0.072 | 0.135 | 0.097 | 0.170 | 0.101 |
| % viable | 90.1 | 91.1 | 89.8 | 93.8 | 96.0 | 95.5 | 93.7 | 100.0 |
| CV | 10.26 | 16.02 | 10.51 | 3.27 | 5.96 | 4.33 | 7.70 | 4.31 |

Example 10

Figure 10:
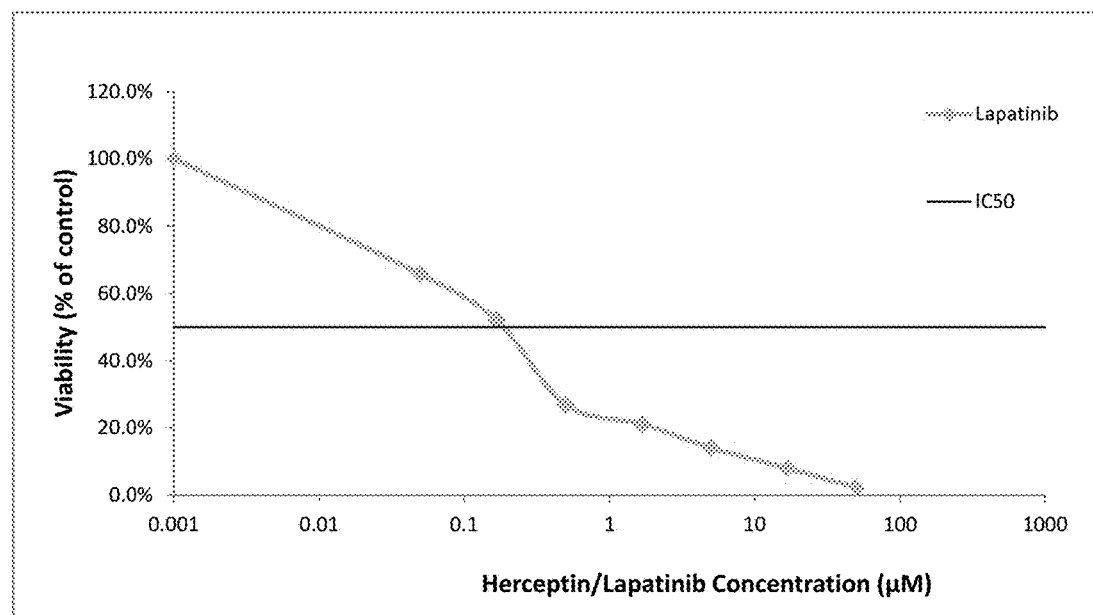
FIG. 10 shows sulforhodamine B (SRB) cell viability assay results from a Herceptin® dose-response analysis of Herceptin®-sensitive BT474 cells. See Table 25.

The $IC_{50}$ of lapatinib was determined for the Herceptin®-sensitive BT474 cell line. Cell culture conditions and cell viability analysis were performed as described in Example 2, except that 5000 cells were plated per well. Unlike in Example 2, however, the cells were subjected to a 72 hour incubation under standard culture conditions in the presence of the concentrations (µM) of lapatinib shown in Table 25. Lapatinib $IC_{50}$ data are also reported in Table 25, and represented graphically in FIG. 10.

TABLE 25

| Lapatinib (µM) | 50 | 16.7 | 5 | 1.67 | 0.5 | 0.167 | 0.05 | 0.001 |
|---|---|---|---|---|---|---|---|---|
| A at 565 nm | 0.035 | 0.137 | 0.240 | 0.383 | 0.415 | 0.909 | 1.082 | 1.655 |
| (in triplicate) | 0.063 | 0.137 | 0.250 | 0.347 | 0.501 | 0.894 | 1.083 | 1.745 |
| background = 0.046 | 0.018 | 0.134 | 0.224 | 0.338 | 0.445 | 0.838 | 1.165 | 1.664 |
| mean A | 0.038 | 0.136 | 0.238 | 0.356 | 0.453 | 0.880 | 1.110 | 1.688 |
| SD | 0.023 | 0.002 | 0.013 | 0.024 | 0.044 | 0.037 | 0.048 | 0.050 |
| % viable | 2.3 | 8.0 | 14.1 | 21.1 | 26.9 | 52.1 | 65.7 | 100.0 |
| CV | 59.45 | 1.28 | 5.52 | 6.70 | 9.63 | 4.25 | 4.29 | 2.94 |

Example 11

LGT-E-Mediated Herceptin® Sensitization Provided by LTG-E Pre-Treatment of Herceptin®-Resistant, HER2-Positive Breast Ductal Carcinoma Line, BT474-TxR.

Figure 11:
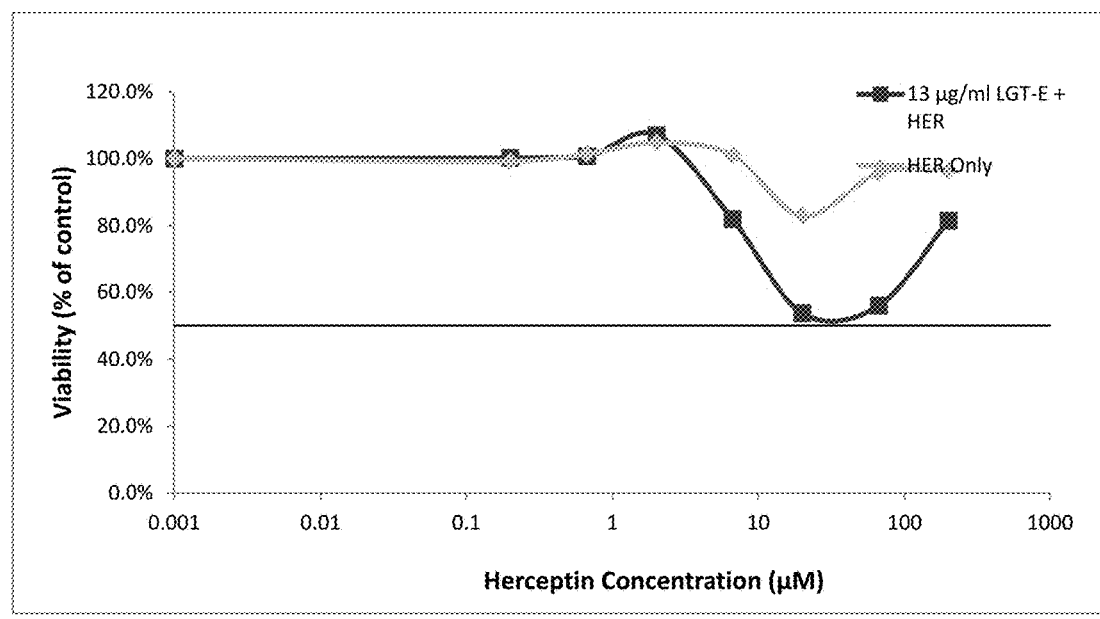
FIG. 11 shows sulforhodamine B (SRB) cell viability assay results from a Herceptin® dose-response analysis of Herceptin®-resistant, HER2-positive breast ductal carcinoma line, BT474-TxR that were pretreated with 13 μg/ml of LGT-E See Tables 26-27.

Using the cell culture methods described in Examples 2 and 9, as adapted for Herceptin® treatment of BT474 cells, the chemosensitizing effect of LTG-E pretreatment on Herceptin®-treated BT474-TxR cells was studied. In this study, cells were pre-treated with 13 µg/ml of LTG-E before treating the cells with 1:3 serially-diluted, 50 µl aliquots of Herceptin® that contained from $1 \times 10^2$ to $1 \times 10^{-3}$ µM of Herceptin®. Table 26 reports the cell viability data relating to pre-treatment with LTG-E prior to Herceptin® treatment. Table 27 reports control data obtained from cells that were not pre-treated with LTG-E prior to Herceptin® treatment. FIG. 11 summarizes the data of Tables 26 and 27 in a graphical format.

TABLE 26

| Trastuzumab (µM) | 200 | 66.7 | 20 | 6.67 | 2 | 0.667 | 0.2 | 0.001 |
|---|---|---|---|---|---|---|---|---|
| A at 565 nm | 1.480 | 1.066 | 1.012 | 1.577 | 1.901 | 1.836 | 1.848 | 1.867 |
| (in triplicate) | 1.555 | 0.986 | 1.011 | 1.533 | 2.098 | 1.939 | 1.955 | 1.909 |
| background = 0.045 | 1.580 | 1.115 | 1.017 | 1.529 | 2.062 | 1.929 | 1.873 | 1.885 |
| mean A | 1.538 | 1.056 | 1.013 | 1.546 | 2.020 | 1.901 | 1.892 | 1.887 |
| SD | 0.052 | 0.065 | 0.004 | 0.027 | 0.105 | 0.057 | 0.056 | 0.021 |
| % viable | 81.5 | 55.9 | 53.7 | 81.9 | 107.1 | 100.8 | 100.3 | 100.0 |
| CV | 3.38 | 6.15 | 0.35 | 1.73 | 5.21 | 2.99 | 2.94 | 1.12 |

TABLE 27

| Trastuzumab (μM) | 200 | 66.7 | 20 | 6.67 | 2 | 0.667 | 0.2 | 0.001 |
|---|---|---|---|---|---|---|---|---|
| A at 565 nm | 2.089 | 1.959 | 1.985 | 2.071 | 2.049 | 1.982 | 1.929 | 1.948 |
| (in triplicate) | 1.811 | 1.803 | 1.461 | 1.980 | 2.106 | 2.058 | 2.096 | 2.050 |
| background = 0.045 | 1.980 | 2.063 | 1.600 | 2.099 | 2.224 | 2.134 | 2.015 | 2.090 |
| mean A | 1.960 | 1.941 | 1.682 | 2.050 | 2.126 | 2.058 | 2.013 | 2.029 |
| SD | 0.140 | 0.131 | 0.272 | 0.062 | 0.089 | 0.076 | 0.084 | 0.073 |
| % viable | 96.6 | 95.7 | 82.9 | 101.0 | 104.8 | 101.4 | 99.2 | 100.0 |
| CV | 7.15 | 6.75 | 16.15 | 3.03 | 4.20 | 3.71 | 4.16 | 3.61 |

Example 12

LGT-E-Mediated Lapatinib Sensitization Provided by LGT-E Pre-Treatment of Herceptin®-Resistant, HER2-Positive Breast Ductal Carcinoma Line, BT474-TxR.

Figure 12A:
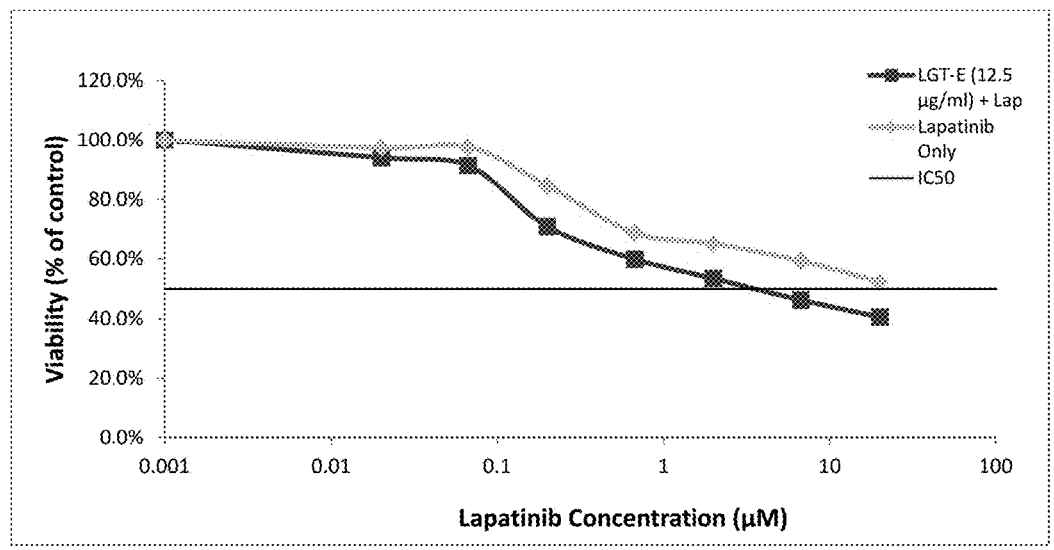
FIG. 12 shows sulforhodamine B (SRB) cell viability assay results from Herceptin®-resistant, HER2-positive breast ductal carcinoma BT474-TxR cells that were pre-treated with (A) 12 μg/ml or (B) 25 μg/ml of LGT-E followed by 72 hours of treatment with various concentrations of lapatinib. See Tables 28-31.
Figure 12B:
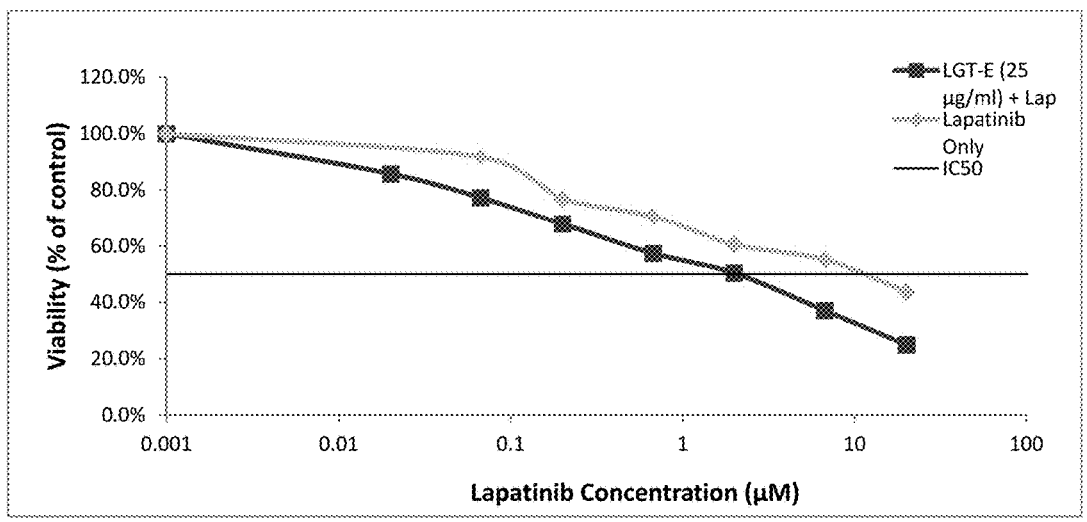

Using the cell culture methods described in Examples 2 and 9, as adapted for BT474 cells, the chemosensitizing effect of LTG-E pretreatment on lapatinib-treated BT474-TxR cells was studied. In this study, cells were pre-treated with 12.5 or 25 μg/ml of LGT-E before treating the cells with 1:3 serially-diluted, 50 μl aliquots of lapatinib that contained from 30 to $1\times10^{-3}$ μM of lapatinib. Tables 28 and 30 report the cell viability data relating to pre-treatment with 12.5 or 25 μg/ml, respectfully, of LGT-E prior to lapatinib treatment. Tables 29 and 31 report respective control data obtained from cells that were not pre-treated with LGT-E prior to lapatinib treatment. FIG. 12 summarizes the data of Tables 51-54 in a graphical format.

TABLE 28

| Lapatinib (μM) | 20 | 6.7 | 2 | 0.67 | 0.2 | 0.067 | 0.02 | 0.001 |
|---|---|---|---|---|---|---|---|---|
| A at 565 nm | 0.416 | 0.512 | 0.526 | 0.594 | 0.738 | 1.024 | 0.898 | 1.048 |
| (in triplicate) | 0.393 | 0.434 | 0.521 | 0.602 | 0.712 | 0.871 | 0.968 | 0.980 |
| background = 0.045 | 0.404 | 0.437 | 0.552 | 0.596 | 0.670 | 0.836 | 0.944 | 0.962 |
| mean A | 0.405 | 0.461 | 0.533 | 0.598 | 0.707 | 0.911 | 0.937 | 0.997 |
| SD | 0.012 | 0.044 | 0.017 | 0.004 | 0.034 | 0.100 | 0.036 | 0.045 |
| % viable | 40.6 | 46.3 | 53.5 | 59.9 | 70.9 | 91.3 | 94.0 | 100.0 |
| CV | 2.84 | 9.58 | 3.12 | 0.70 | 4.85 | 10.98 | 3.80 | 4.55 |

TABLE 29

| Lapatinib (μM) | 20 | 6.7 | 2 | 0.67 | 0.2 | 0.067 | 0.02 | 0.001 |
|---|---|---|---|---|---|---|---|---|
| A at 565 nm | 0.598 | 0.677 | 0.726 | 0.742 | 0.932 | 1.043 | 1.054 | 1.137 |
| (in triplicate) | 0.616 | 0.677 | 0.717 | 0.752 | 0.956 | 1.126 | 1.125 | 1.085 |
| background = 0.045 | 0.567 | 0.667 | 0.774 | 0.844 | 0.993 | 1.151 | 1.132 | 1.181 |
| mean A | 0.594 | 0.674 | 0.739 | 0.780 | 0.961 | 1.107 | 1.104 | 1.135 |
| SD | 0.025 | 0.006 | 0.031 | 0.056 | 0.031 | 0.057 | 0.043 | 0.048 |
| % viable | 52.3 | 59.4 | 65.2 | 68.7 | 84.7 | 97.6 | 97.3 | 100.0 |
| CV | 4.17 | 0.86 | 4.15 | 7.21 | 3.20 | 5.11 | 3.91 | 4.24 |

TABLE 30

| Lapatinib (μM) | 20 | 6.7 | 2 | 0.67 | 0.2 | 0.067 | 0.02 | 0.001 |
|---|---|---|---|---|---|---|---|---|
| A at 565 nm | 0.264 | 0.337 | 0.485 | 0.654 | 0.762 | 0.953 | 1.016 | 1.041 |
| (in triplicate) | 0.222 | 0.413 | 0.516 | 0.483 | 0.640 | 0.664 | 0.749 | 0.939 |
| background = 0.047 | 0.231 | 0.316 | 0.447 | 0.512 | 0.548 | 0.603 | 0.699 | 0.893 |
| mean A | 0.239 | 0.355 | 0.482 | 0.549 | 0.650 | 0.740 | 0.821 | 0.957 |
| SD | 0.022 | 0.051 | 0.035 | 0.092 | 0.107 | 0.187 | 0.170 | 0.076 |
| % viable | 24.9 | 37.1 | 50.4 | 57.4 | 67.9 | 77.3 | 85.8 | 100.0 |
| CV | 9.27 | 14.38 | 7.17 | 16.66 | 16.53 | 25.28 | 20.76 | 7.91 |

TABLE 31

| Lapatinib (μM) | 20 | 6.7 | 2 | 0.67 | 0.2 | 0.067 | 0.02 | 0.001 |
|---|---|---|---|---|---|---|---|---|
| A at 565 nm | 0.530 | 0.647 | 0.779 | 0.881 | 0.933 | 1.148 | 1.021 | 1.160 |
| (in triplicate) | 0.445 | 0.604 | 0.673 | 0.818 | 0.841 | 1.073 | 0.968 | 1.147 |
| background = 0.047 | 0.571 | 0.694 | 0.686 | 0.790 | 0.941 | 1.017 | 0.924 | 1.221 |
| mean A | 0.515 | 0.648 | 0.712 | 0.829 | 0.905 | 1.079 | 0.971 | 1.176 |
| SD | 0.064 | 0.045 | 0.058 | 0.047 | 0.056 | 0.066 | 0.049 | 0.040 |
| % viable | 43.8 | 55.1 | 60.6 | 70.5 | 76.9 | 91.8 | 82.6 | 100.0 |
| CV | 12.48 | 6.95 | 8.12 | 5.62 | 6.14 | 6.09 | 5.00 | 3.36 |

Example 13

Figure 13:
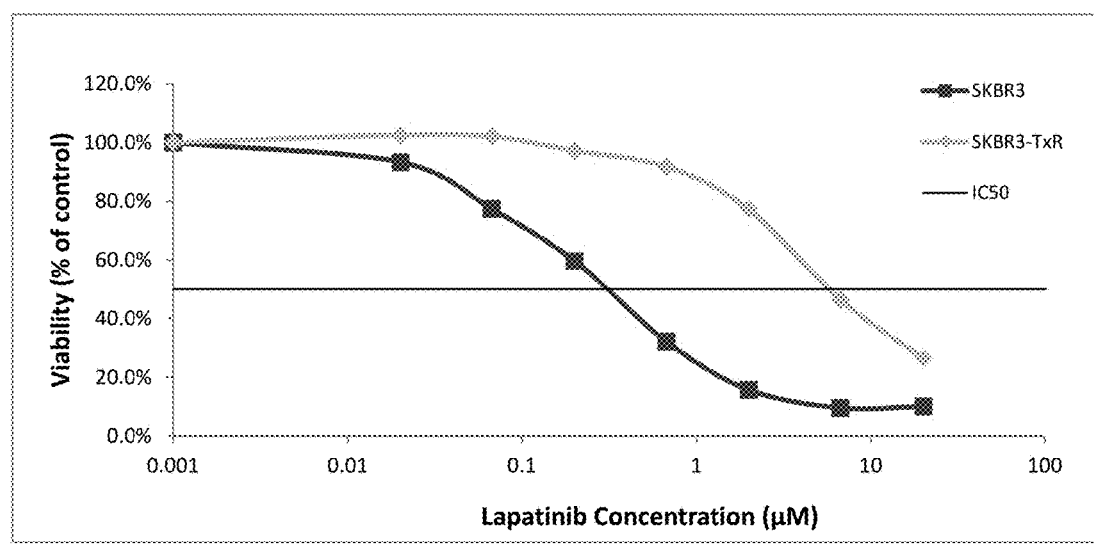
FIG. 13 shows sulforhodamine B (SRB) cell viability assay results from a lapatinib dose response analysis of lapatinib sensitivity of lapatinib-senstive HER2-positive breast adenocarcinoma line, SkBr3, to that of its lapatinib-resistant sub-line SkBr3-TxR. See Tables 32-33.

A comparison of the lapatinib sensitivity of lapatinib-senstive HER2-positive breast adenocarcinoma line, SkBr3, to that of its lapatinib-resistant subline. To determine the degree to which the lapatinib-resistant cell lines were more resistant to lapatinib than their respective parental lapatinib-sensitive cell lines, cell viabilities of the lapatinib-resistant SkBr3-TxR cell line and the lapatinib-sensitive cell line from which SkBr3-TxR was derived, SkBr3, were compared following lapatinib treatment in the absence of a chemosensitizing pre-treatment step. Cell culture conditions and cell viability analysis were performed as described in Example 2. As in Example 2, cells were treated with 50 µl aliquots that contained 20, 6.7, 2, 0.7, 0.2, 0.07, or 0.02 µM of lapatinib. Tables 32 and 33 show the lapatinib dose-response in SkBr3 and SkBr3-TxR lines, respectively. FIG. 13 summarizes the data of Tables 32-33 in a graphical format.

TABLE 32

| Lapatinib (µM) | 20 | 6.7 | 2 | 0.67 | 0.2 | 0.067 | 0.02 | 0.001 |
|---|---|---|---|---|---|---|---|---|
| A at 565 nm | 0.220 | 0.206 | 0.344 | 0.738 | 1.325 | 1.710 | 2.038 | 2.216 |
| (in triplicate) | 0.215 | 0.198 | 0.331 | 0.681 | 1.255 | 1.681 | 1.934 | 2.145 |
| background = 0.047 | 0.228 | 0.228 | 0.365 | 0.705 | 1.362 | 1.729 | 2.195 | 2.247 |
| mean A | 0.221 | 0.211 | 0.347 | 0.708 | 1.314 | 1.707 | 2.056 | 2.203 |
| SD | 0.007 | 0.016 | 0.017 | 0.029 | 0.054 | 0.024 | 0.131 | 0.052 |
| % viable | 10.1 | 9.6 | 15.8 | 32.2 | 59.7 | 77.5 | 93.3 | 100.0 |
| CV | 2.96 | 7.36 | 4.94 | 4.04 | 4.13 | 1.42 | 6.39 | 2.37 |

TABLE 33

| Lapatinib (µM) | 20 | 6.7 | 2 | 0.67 | 0.2 | 0.067 | 0.02 | 0.001 |
|---|---|---|---|---|---|---|---|---|
| A at 565 nm | 0.605 | 1.117 | 1.754 | 2.086 | 2.205 | 2.350 | 2.341 | 2.244 |
| (in triplicate) | 0.599 | 1.069 | 1.781 | 2.177 | 2.233 | 2.314 | 2.390 | 2.301 |
| background = 0.047 | 0.615 | 1.012 | 1.790 | 2.063 | 2.264 | 2.370 | 2.340 | 2.349 |
| mean A | 0.607 | 1.066 | 1.775 | 2.109 | 2.234 | 2.345 | 2.357 | 2.298 |
| SD | 0.008 | 0.053 | 0.019 | 0.060 | 0.030 | 0.028 | 0.029 | 0.053 |
| % viable | 26.4 | 46.4 | 77.2 | 91.8 | 97.2 | 102.0 | 102.6 | 100.0 |
| CV | 1.33 | 4.93 | 1.06 | 2.86 | 1.32 | 1.21 | 1.21 | 2.29 |

Example 14

LGT-E-Mediated Lapatinib Sensitization Provided by LGT-E Pre-Treatment of Herceptin® and Lapatinib-Resistant, HER2-Positive Breast Adenocarcinoma Line, SkBr3-TxR.

Figure 14:
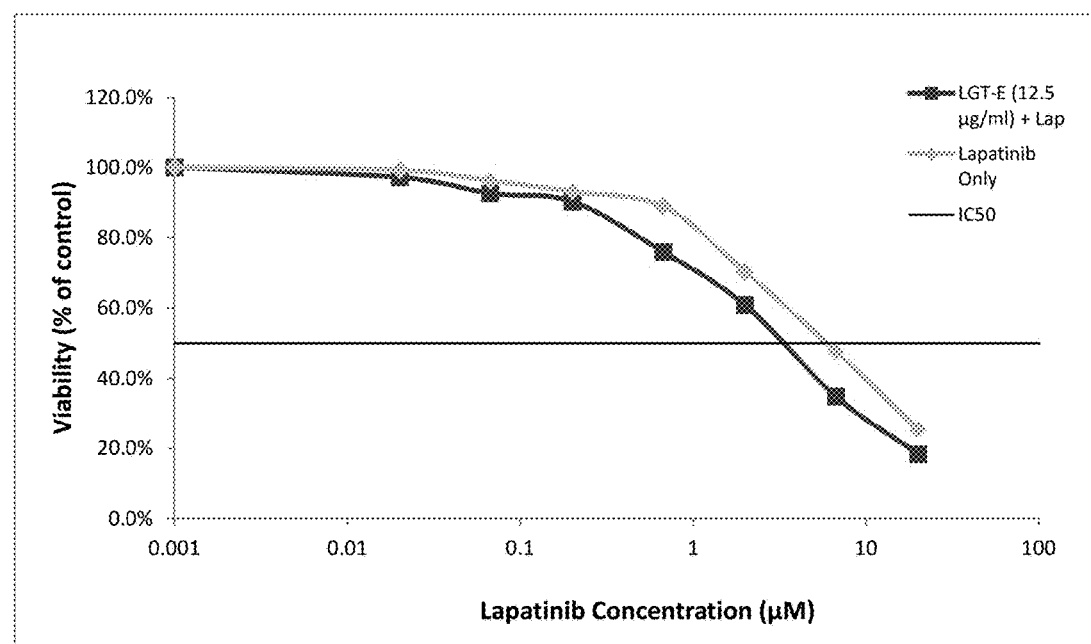
FIG. 14 shows sulforhodamine B (SRB) cell viability assay results from lapatinib-resistant HER2-positive breast adenocarcinoma SkBr3-TxR cells that were pre-treated with 12.5 μg/ml of LGT-E followed by 72 hours of treatment with various concentrations of lapatinib. See Tables 34-35.

Using the cell culture methods described in Examples 2, with the exception that 5000 SkBr3-TxR cells were plated per well, the chemosensitizing effect of LGT-E on lapatinib-treated SkBr3-TxR cells was studied. In this study, cells were pre-treated with 12.5 µg/ml of LGT-E before treating the cells with 50 µl aliquots of lapatinib that contained from 20, 6.7, 2, 0.7, 0.2, 0.07, or 0.02 µM of lapatinib. Table 34 reports the cell viability data relating to pre-treatment. Table 35 reports control data obtained from cells that were not pre-treated with LGT-E prior to lapatinib treatment. FIG. 14 summarizes the data of Tables 34 and 35 in a graphical format.

TABLE 34

| Lapatinib (µM) | 20 | 6.7 | 2 | 0.67 | 0.2 | 0.067 | 0.02 | 0.001 |
|---|---|---|---|---|---|---|---|---|
| A at 565 nm | 0.424 | 0.810 | 1.378 | 1.679 | 2.042 | 2.101 | 2.109 | 2.226 |
| (in triplicate) | 0.435 | 0.716 | 1.235 | 1.652 | 1.967 | 1.939 | 2.223 | 2.238 |
| background = 0.044 | 0.358 | 0.790 | 1.431 | 1.712 | 1.986 | 2.111 | 2.121 | 2.177 |
| mean A | 0.406 | 0.772 | 1.348 | 1.681 | 1.999 | 2.051 | 2.151 | 2.214 |
| SD | 0.042 | 0.050 | 0.101 | 0.030 | 0.039 | 0.097 | 0.063 | 0.032 |
| % viable | 18.3 | 34.9 | 60.9 | 75.9 | 90.3 | 92.6 | 97.2 | 100.0 |
| CV | 1.33 | 4.93 | 1.06 | 2.86 | 1.32 | 1.21 | 1.21 | 2.29 |

TABLE 35

| Lapatinib (µM) | 20 | 6.7 | 2 | 0.67 | 0.2 | 0.067 | 0.02 | 0.001 |
|---|---|---|---|---|---|---|---|---|
| A at 565 nm | 0.481 | 1.124 | 1.684 | 2.067 | 2.083 | 2.181 | 2.233 | 2.324 |
| (in triplicate) | 0.657 | 1.068 | 1.543 | 2.071 | 2.223 | 2.213 | 2.287 | 2.289 |

TABLE 35-continued

| Lapatinib (µM) | 20 | 6.7 | 2 | 0.67 | 0.2 | 0.067 | 0.02 | 0.001 |
|---|---|---|---|---|---|---|---|---|
| background = 0.044 | 0.612 | 1.092 | 1.613 | 1.974 | 2.100 | 2.225 | 2.306 | 2.267 |
| mean A | 0.584 | 1.095 | 1.614 | 2.038 | 2.136 | 2.207 | 2.276 | 2.294 |
| SD | 0.091 | 0.028 | 0.071 | 0.055 | 0.076 | 0.023 | 0.038 | 0.029 |
| % viable | 25.4 | 47.7 | 70.4 | 88.8 | 93.1 | 96.2 | 99.2 | 100.0 |
| CV | 15.67 | 2.57 | 4.37 | 2.69 | 3.58 | 1.03 | 1.66 | 1.25 |

Example 15

No LGT-E-Mediated Increase in Sensitization to Daunorubicin in the Daunorubicin-Sensitive Myelogenous Leukemia Line K562.

Figure 15:
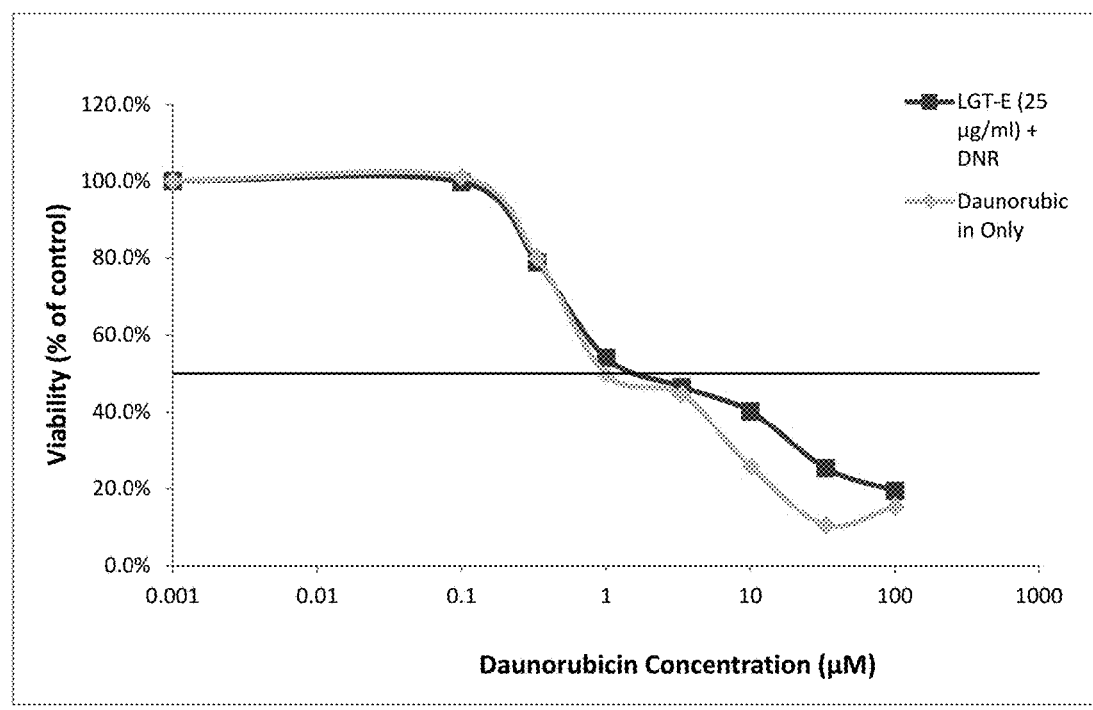
FIG. 15 shows sulforhodamine B (SRB) cell viability assay results from daunorubicin-sensitive myelogenous leukemia K562 cells that were pre-treated with 25 μg/ml of LGT-E followed by 72 hours of treatment with various concentrations of daunorubicin. See Tables 36-37.

Using the cell culture methods described in Example 2, the chemosensitizing effect of LTG-E on daunorubicin-treated K562 cells was studied. In this study, cells were pre-treated with 25 µg/ml of LGT-E before treating the cells with 1:3 serially-diluted, 50 µl aliquots that contained from 30 to $1 \times 10^{-3}$ µM of daunorubicin. Table 36 reports the cell viability data relating to pre-treatment with LTG-E prior to daunorubicin treatment. Table 37 reports control data obtained from cells that were not pre-treated with LGT-E prior to daunorubicin treatment. FIG. 15 summarizes the data of Tables 36 and 37 in a graphical format.

TABLE 36

| Docetaxel (nM) | 100 | 33.3 | 10 | 3.33 | 1 | 0.333 | 0.1 | 0.001 |
|---|---|---|---|---|---|---|---|---|
| A at 516 nm | 0.585 | 0.854 | 1.422 | 1.304 | 1.534 | 2.283 | 2.837 | 2.851 |
| (in triplicate) | 0.483 | 0.723 | 1.266 | 1.458 | 1.612 | 2.210 | 2.840 | 2.863 |
| background = 0.044 | 0.591 | 0.591 | 0.756 | 1.229 | 1.493 | 2.277 | 2.875 | 2.864 |
| mean A | 0.553 | 0.723 | 1.148 | 1.331 | 1.547 | 2.257 | 2.851 | 2.860 |
| SD | 0.061 | 0.132 | 0.348 | 0.117 | 0.060 | 0.041 | 0.021 | 0.007 |
| % viable | 19.3 | 25.3 | 40.2 | 46.5 | 54.1 | 78.9 | 99.7 | 100.0 |
| CV | 10.97 | 18.19 | 30.34 | 8.77 | 3.91 | 1.80 | 0.74 | 0.25 |

TABLE 37

| Docetaxel (nM) | 100 | 33.3 | 10 | 3.33 | 1 | 0.333 | 0.1 | 0.001 |
|---|---|---|---|---|---|---|---|---|
| A at 565 nm | 0.496 | 0.422 | 1.057 | 1.275 | 1.512 | 2.242 | 2.858 | 2.840 |
| (in triplicate) | 0.387 | 0.204 | 0.327 | 1.259 | 1.379 | 2.353 | 2.899 | 2.853 |
| background = 0.044 | 0.424 | 0.272 | 0.812 | 1.272 | 1.350 | 2.227 | 2.863 | 2.839 |
| mean A | 0.436 | 0.300 | 0.732 | 1.269 | 1.414 | 2.274 | 2.874 | 2.844 |
| SD | 0.055 | 0.112 | 0.372 | 0.009 | 0.086 | 0.069 | 0.022 | 0.008 |
| % viable | 15.3% | 10.5% | 25.7% | 44.6% | 49.7% | 80.0% | 101.0% | 100.0% |
| CV | 12.72% | 37.24% | 50.74% | 0.67% | 6.11% | 3.03% | 0.78% | 0.27% |

Example 16

Figure 16:
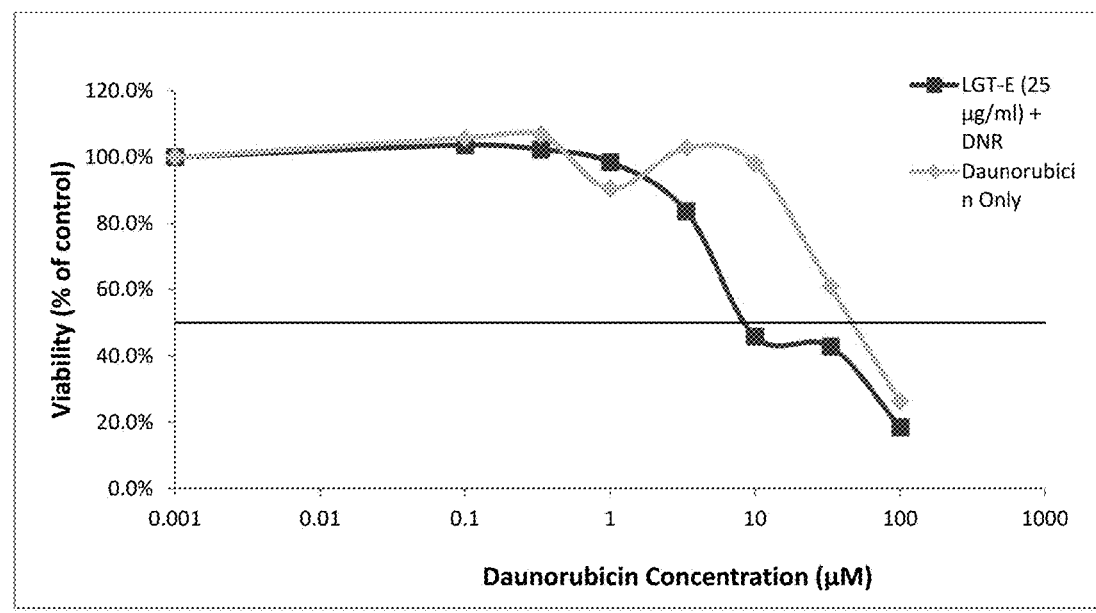
FIG. 16 shows sulforhodamine B (SRB) cell viability assay results from daunorubicin-resistant myelogenous leukemia K562/Dox cells that were pre-treated with 25 μg/ml of LGT-E followed by 72 hours of treatment with various concentrations of daunorubicin. See Tables 38-39.

LGT-E-mediated increase in sensitization to daunorubicin in daunorubicin-resistant myelogenous leukemia lines K562/Dox. Using the cell culture methods described in Example 2, the chemosensitizing effect of LGT-E on daunorubicin-treated K562/Dox cells was studied. In this study, cells were pre-treated with 25 µg/ml of LGT-E before treating the cells with 1:3 serially-diluted, 50 µl aliquots that contained from 30 to 1×10−3 µM of daunorubicin. Table 38 reports the cell viability data relating to pre-treatment with LGT-E prior to daunorubicin treatment. Table 39 reports control data obtained from cells that were not pre-treated with LGT-E prior to daunorubicin treatment. FIG. 16 summarizes the data of Tables 38 and 39 in a graphical format.

TABLE 38

| Docetaxel (nM) | 100 | 33.3 | 10 | 3.33 | 1 | 0.333 | 0.1 | 0.001 |
|---|---|---|---|---|---|---|---|---|
| A at 565 nm | 0.563 | 1.165 | 0.870 | 2.389 | 2.722 | 2.812 | 2.817 | 2.905 |
| (in triplicate) | 0.412 | 1.137 | 1.328 | 2.339 | 2.740 | 2.816 | 2.864 | 2.838 |
| background = 0.043 | 0.557 | 1.223 | 1.581 | 2.174 | 2.657 | 2.805 | 2.863 | 2.499 |
| mean A | 0.510 | 1.175 | 1.259 | 2.300 | 2.706 | 2.811 | 2.848 | 2.747 |
| SD | 0.086 | 0.044 | 0.360 | 0.113 | 0.044 | 0.006 | 0.027 | 0.218 |
| % viable | 18.6 | 42.8 | 45.8 | 83.7 | 98.5 | 102.3 | 103.7 | 100.0 |
| CV | 16.75 | 3.73 | 28.62 | 4.89 | 1.61 | 0.20 | 0.94 | 7.92 |

TABLE 39

| Docetaxel (nM)     | 100   | 33.3  | 10    | 3.33  | 1     | 0.333 | 0.1   | 0.001 |
|--------------------|-------|-------|-------|-------|-------|-------|-------|-------|
| A at 565 nm        | 0.703 | 1.683 | 2.731 | 2.863 | 2.395 | 2.962 | 2.914 | 2.653 |
| (in triplicate)    | 0.775 | 1.716 | 2.740 | 2.847 | 2.620 | 2.951 | 2.918 | 2.827 |
| background = 0.043 | 0.691 | 1.652 | 2.678 | 2.834 | 2.512 | 2.967 | 2.967 | 2.835 |
| mean A             | 0.723 | 1.683 | 2.716 | 2.848 | 2.509 | 2.960 | 2.933 | 2.771 |
| SD                 | 0.045 | 0.032 | 0.034 | 0.015 | 0.113 | 0.008 | 0.030 | 0.103 |
| % viable           | 26.1  | 60.7  | 98.0  | 102.8 | 90.5  | 106.8 | 105.8 | 100.0 |
| CV                 | 16.75 | 3.73  | 28.62 | 4.89  | 1.61  | 0.20  | 0.94  | 7.92  |

Example 17

LGT-E is an Effective Chemosensitizor for Docetaxel In Vivo.

Based on the results that showed LGT-E to be a chemosensitizer for docetaxel, in vivo studies were designed to assess the effectiveness of orally-administered LGT-E on the chemotherapeutic effect of Docetaxel. With that goal in mind, the oral maximum tolerated dose (MTD) in CD-1 mice (Charles River Laboratories International, Inc. Wilmington, Mass.) was determined by administering escalating single, once-only, oral doses of 100, 250, 500, 750, and 1000 mg/kg, as well as daily doses of 62.5, 125, 250, or 500 mg/kg over the course of 7 days. Specifically, the MTD was defined as the dose that: (i) was nonfatal; (ii) caused no more than a 10% retardation of body weight gain as compared to control animals; and (iii) did not cause overt organ dysfunction or side effects. In the cases of both the single and multiple dose approaches, the MTD was around 500 mg/kg.

Subsequent to identifying the MTD for LTG-E, the anti-tumor effect of LGT-E (500 mg/kg, oral gavage) administered in combination with docetaxel (20 mg/kg, i.v.) was compared to docetaxel treatment alone. More particularly, these studies involved the use of six severe combined immunodeficient (SCID) male mice (Taconic Farms, Inc. Oxnard, Calif.) that weighed from 15 to 20 g, were between 4-6 weeks old, and that had been housed in cages with HEPA-filtered air (12-hr light/dark cycle). Tumors were caused to form in the mice by subcutaneously injecting PC3 and PC3-TxR cells into the mice. To perform the cell injections, PC3 and PC3-TxR cells were first separately suspended in a 1:1 mixture of Matrigel (BD Biosciences, Franklin Lakes, N.J., U.S.A.) and RPMI 1640 (Mediatech, Manassas, Va., or Life Technologies Grand Island, N.Y.). Then the cells were subcutaneously implanted into flanks of mice via injection. Mice that had consistently shown tumor growth for 19 days following the injection of the cells were used in the tumor studies. More specifically, these studies were initiated when the xenograft tumors reached a volume of about 120 mm$^3$, calculated by using the formula for a semiellipoid, i.e., Volume=Width$^2$×(Length/2).

Figure 17A:
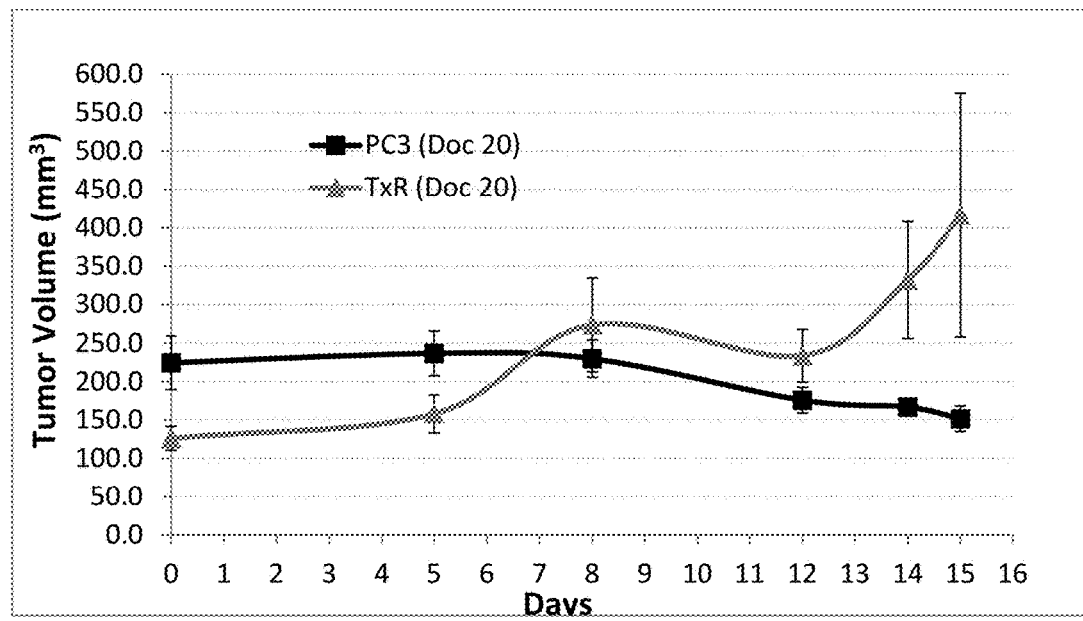
FIG. 17A relates the docetaxel-resistance of PC3-TxR cell tumors versus docetaxel-sensitive PC3-ATCC cell tumors in SCID mice tumor hosts to tumor size over the course of a 15 day treatment period with 20 mg/kg body weight of docetaxel, beginning with docetaxel administration at day 0 is the first day of Doc treatment.
Figure 17B:
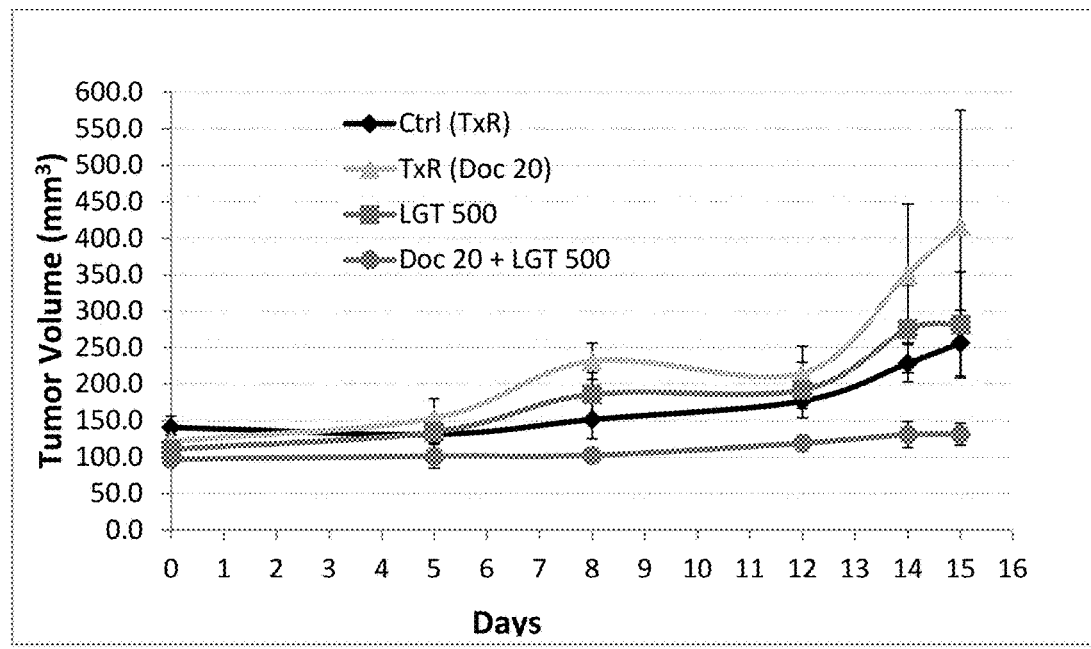
FIG. 17B relates the chemosensitizing effect of LGT-E (500 mg/kg body weight) with respect to docetaxel treatment of PC3-TxR tumors, using the PC3-TxR tumor model described in FIG. 17A, including untreated tumors, LGT-E-treated tumors, and LGT-E and docetaxel-treated tumors.

A tumor study was performed in accordance with the basic methodologies described above to measure changes in the tumor sizes of each mouse over a 15 day time course, beginning on the first day of treatment. The tumor-containing mice in the study were randomized into six groups: Group (1) mice had PC3 cell tumor xenografts, and were treated only with Docetaxel (20 mg/kg, intravenously (IV), once per week, n=9) and Group (2) mice had PC3-TxR cell tumor xenografts, and were not treated at all (n=7). Changes in the tumor sizes of Groups (1) and (2) over the course of the study are shown in FIG. 17A. Group (3) mice had PC3-TxR cell tumor xenografts, and were treated with Docetaxel (20 mg/kg, IV, once per week, n=8); Group (4) mice had PC3-TxR cell tumor xenografts, and were treated with LTG-E (500 mg/kg, via oral gavage (PO), daily, n=8); Group (5) mice had PC3-TxR cell tumor xenografts, and were treated with Docetaxel (20 mg/kg, IV, once per week) and LTG-E (250 mg/kg, PO, daily) (n=8); and Group (6) mice had PC3-TxR cell tumor xenografts, and were treated with Docetaxel 20 mg/kg (IV, once per week) and LTG-E (500 mg/kg, PO, daily) (n=9). Changes in the tumor sizes of Groups (3-6) over the course of the study are shown in FIG. 17B.

Changes in the tumor sizes of Group (1) and Group (2) over the course of the study are shown in FIG. 17A, which indicated that both PC3 and PC3-TxR cells were successfully grown in the SCID mice. Changes in tumor size of Group (3-6) over the time course of the study are shown in FIG. 17B. LGT-E alone did not show any anti-tumor effect, but significantly enhanced the docetaxel's anti-tumor effect as compared to the docetaxel-only group.

REFERENCES

Chow M, and Huang Y. "Utilizing Chinese Medicines to Improve Cancer Therapy-Fiction or Reality?" Current Drug Discovery Technologies, 2010.

Huang Y, and Sadee W. (2003). Drug sensitivity and resistance genes in cancer chemotherapy: a chemogenomics approach. Drug Discov Today 8, 356-363.

Huang Y., and Sadee W. (2006). Membrane transporters and channels in chemoresistance and sensitivity of tumor cells. Cancer Lett 239, 168-182.

Huang Y, et al. (2004). Membrane transporters and channels: role of the transportome in cancer chemosensitivity and chemoresistance. Cancer Res 64, 4294-4301.

Huang Y, et al. (2005a). Correlating gene expression with chemical scaffolds of cytotoxic agents: ellipticines as substrates and inhibitors of MDR1. Pharmacogenomics J 5, 112-125.

Huang Y, et al. (2005b). Cystine-glutamate transporter SLC7 A 11 in cancer chemosensitivity and chemoresistance. Cancer Res 65, 7446-7454.

Makarovskiy, A N et al. (2002). Survival of docetaxel-resistant prostate cancer cells in vitro depends on phenotype alterations and continuity of drug exposure. Cell Mol Life Sci 59, 1198-1211.

Pon D, et al. "Harnessing traditional Chinese medicine to improve cancer therapy: issues for future development". Therapeutic Delivery 2010; 1:335-344.

Salzberg M, et al. (2007). An open-label, noncomparative phase II trial to evaluate the efficacy and safety of docetaxel in combination with gefitinib in patients with hormone-refractory metastatic prostate cancer, Onkologie 30, 355-360.

Seruga B., et al. (2010). Drug resistance in metastatic castration-resistant prostate cancer. Nat Rev Clin Oncol.

Singh A, et al. (2010). Expression of ABCG2 (BCRP) is regulated by Nrf2 in cancer cells that confers side population and chemoresistance phenotype. Mol Cancer Ther 9, 2365-2376.

Sirotnak F M, et al. (2000). Efficacy of cytotoxic agents against human tumor xenografts is markedly enhanced by coadministration of ZD1839 (Iressa), an inhibitor of EGFR tyrosine kinase. Clin Cancer Res 6, 4885-4892.

Wang Z., et al. (2010). Transporter-mediated multidrug resistance and its modulation by Chinese medicines and other herbal products. Curr Drug Discovery Technologies 1:54-56

Wang Z., et al. (2011) An Improved Method for Evaluation of Chemosensitizing Effect from Herb-Drug Combination—Example with *Tripterygium wilfordii*. Abstract Presented 8th International Conference of Society for Integrative Oncology, Cleveland, November 10-12.

Zhang P, et al. (2010). Loss of Kelch-like ECH-associated protein 1 function in prostate cancer cells causes chemoresistance and radioresistance and promotes tumor growth. Mol Cancer Ther 9, 336-346.

The claimed invention is:

1. A method of treating a cancer comprising the step of: administering to a patient in need thereof a combination of (a) an organic solvent extract of *Tripterygium wilfordii* and (b) a chemotherapeutic drug, wherein (a) and (b) are administered in a combined amount effective to treat the cancer, wherein the cancer is at least in part resistant to treatment by the chemotherapeutic drug (b) alone, wherein the organic solvent extract is an ethanol extract, and wherein at least a portion of (a) is administered prior to administration of (b).

2. A method of claim 1, wherein the ethanol extract is identifiable by the MS/LC chromatogram as described in FIG. 2.

3. A method of claim 1, wherein the cancer is breast cancer, leukemia or prostate cancer.

4. A method of claim 1, wherein the chemotherapeutic drug (b) is selected from the group of docetaxel, daurorubicin, trastuzumab, and lapatinib.

5. A method of claim 1, wherein (a) is administered in an amount to increase (b)'s efficacy over the efficacy of (b) when administered alone.

* * * * *